(12) United States Patent
Truckai et al.

(10) Patent No.: US 11,707,190 B1
(45) Date of Patent: Jul. 25, 2023

(54) MEDICAL ROBOTIC SYSTEM

(71) Applicant: Meditrina, Inc., San Jose, CA (US)

(72) Inventors: Csaba Truckai, Saratoga, CA (US); John H. Shadduck, Menlo Park, CA (US); Akos Toth, Cupertino, CA (US)

(73) Assignee: Meditrina, Inc., San Jose, CA (US)

( * ) Notice: Subject to any disclaimer, the term of this patent is extended or adjusted under 35 U.S.C. 154(b) by 0 days.

(21) Appl. No.: 17/804,428

(22) Filed: May 27, 2022

(51) Int. Cl.
| | | |
|---|---|---|
| *A61B 1/303* | (2006.01) |
| *A61B 1/00* | (2006.01) |
| *A61B 34/37* | (2016.01) |
| *A61B 1/018* | (2006.01) |
| *A61B 17/42* | (2006.01) |
| *A61B 17/32* | (2006.01) |
| *A61B 1/05* | (2006.01) |
| *A61B 90/00* | (2016.01) |
| *A61B 34/30* | (2016.01) |

(52) U.S. Cl.
CPC .......... *A61B 1/303* (2013.01); *A61B 1/00149* (2013.01); *A61B 1/018* (2013.01); *A61B 1/05* (2013.01); *A61B 17/32002* (2013.01); *A61B 17/4241* (2013.01); *A61B 34/37* (2016.02); *A61B 2017/4225* (2013.01); *A61B 2034/301* (2016.02); *A61B 2034/302* (2016.02); *A61B 2090/065* (2016.02)

(58) Field of Classification Search
CPC ..... A61B 1/303; A61B 1/00149; A61B 1/018; A61B 1/05; A61B 17/32002; A61B 17/4241; A61B 34/37; A61B 2017/4225; A61B 2034/301; A61B 2034/302; A61B 2090/065
See application file for complete search history.

(56) References Cited

U.S. PATENT DOCUMENTS

| | | | |
|---|---|---|---|
| 10,433,717 B1 | 10/2019 | Truckai et al. | |
| 11,259,695 B2 | 3/2022 | Truckai et al. | |
| 2002/0022870 A1* | 2/2002 | Truckai | A61B 18/1485 607/101 |
| 2003/0125716 A1* | 7/2003 | Wang | B25J 9/1689 606/1 |
| 2003/0176766 A1* | 9/2003 | Long | A61B 1/0014 600/106 |
| 2008/0154090 A1* | 6/2008 | Hashimshony | A61B 1/018 600/101 |
| 2008/0249553 A1* | 10/2008 | Gruber | A61B 17/32053 606/171 |
| 2009/0082622 A1* | 3/2009 | Takekoshi | A61B 1/015 600/104 |
| 2009/0312600 A1* | 12/2009 | Sholev | A61B 1/317 600/102 |
| 2010/0274078 A1* | 10/2010 | Kim | A61B 34/30 600/102 |
| 2010/0331859 A1* | 12/2010 | Omori | A61B 34/37 606/130 |
| 2018/0326144 A1 | 11/2018 | Truckai | |
| 2019/0142247 A1* | 5/2019 | Maeda | A61B 1/018 600/106 |
| 2019/0282073 A1 | 9/2019 | Truckai | |
| 2020/0000326 A1 | 1/2020 | Truckai et al. | |

(Continued)

*Primary Examiner* — Richard G Louis
(74) *Attorney, Agent, or Firm* — Levine Bagade Han LLP

(57) ABSTRACT

Robotic surgical systems configured to control the movement and actuation of a single robotic arm, and the movement and actuation of multiple tools carried at a distal end of the robotic arm.

18 Claims, 18 Drawing Sheets

(56) References Cited

U.S. PATENT DOCUMENTS

2020/0329953 A1   10/2020   Truckai
2021/0401275 A1   12/2021   Toth et al.
2022/0015620 A1    1/2022   Truckai et al.

* cited by examiner

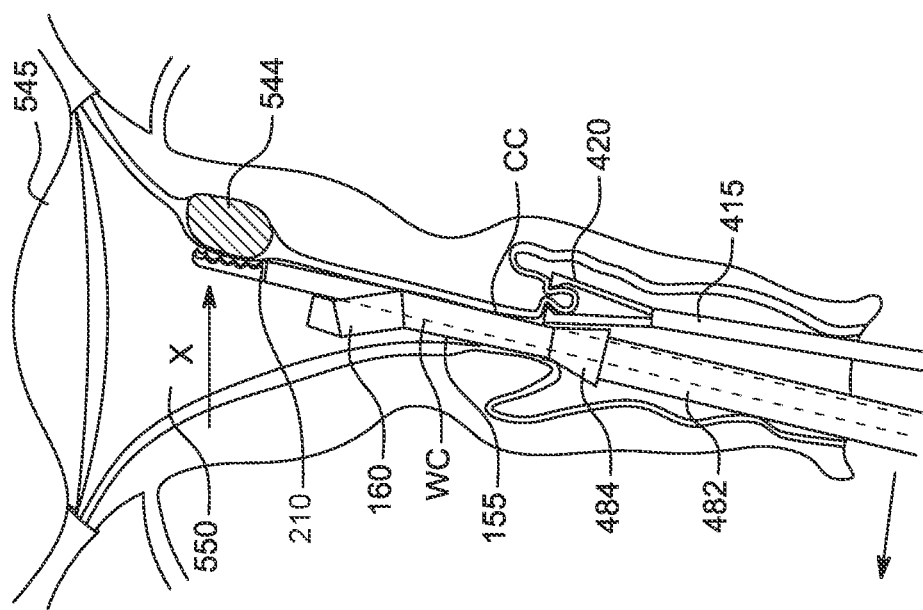
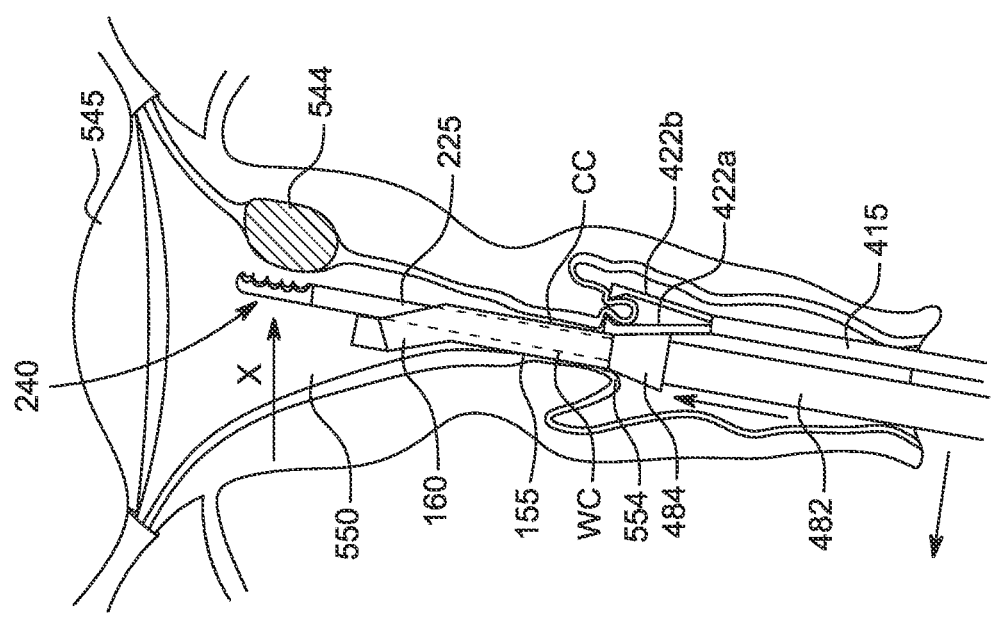

MEDICAL ROBOTIC SYSTEM

BACKGROUND

The present invention is related to a robotic surgical system that is configured to control the movement and actuation of a single robotic arm and the movement and actuation of multiple tools in a gynecology procedure.

SUMMARY

The principles of the present disclosure relate to medical robotic systems. For example, some aspects of the techniques described herein relate to medical robot systems including: a robotic arm having a plurality of moveable arm segments; an endoscopic viewing assembly detachably coupled to a distal segment of the robotic arm, the endoscopic viewing assembly having an elongate endoscope shaft extending about a longitudinal axis to a distal end carrying an image sensor; and a stabilizing device detachably coupled to a distal segment of the robotic arm, the stabilizing device having an elongate tool shaft extending about a longitudinal axis adapted for engaging tissue to stabilize a cervix of a patient.

Variations of a medical robot system can further include a motor drive configured to manipulate various implements on the medical robotic system. For example, the motor drive can rotate the elongate endoscope shaft relative to its longitudinal axis. The motor drive can also be configured to move the elongate endoscope shaft axially relative to its longitudinal axis.

Additionally, the motor drive is configured to rotate the elongate tool shaft relative to its longitudinal axis. The motor drive can also be configured to move the elongate tool shaft axially relative to its longitudinal axis.

In some aspects, the techniques described herein relate to a medical robot system further including a treatment tool detachably coupled to a distal segment of the robotic arm, the treatment tool having a treatment tool shaft extending about a longitudinal axis to a working end, wherein the treatment tool shaft is configured for introduction through the working channel of the endoscopic viewing assembly.

Motor drives of the present robotic system can be configured to rotate the treatment tool shaft relative to its longitudinal axis and/or move the treatment tool shaft axially relative to its longitudinal axis. Examples of such treatment tools include, but are not limited to, a resection device, ablation device, coagulation device, biopsy device and dissection device.

In additional variations the treatment tool includes a resection device with a moving cutting member, and wherein the system includes a resecting motor drive for moving the moving cutting member, which moves at least rotationally or axially.

Variations of the medical robot system include a cervical canal sealing assembly coupled to at least one of the robotic arms and the endoscopic viewing assembly. In additional variations a distal end of the cervical canal sealing assembly includes a cervical seal configured for movement co-axially with a medial portion of the elongate endoscope shaft.

Additionally, the present robotic system can include motor drives that are adapted for moving the cervical seal. Variations of the system include a contact sensor carried by the cervical seal adapted to sense contact with a cervix of the patient and send signals of the contact or lack thereof to a controller. In additional variations, the medical robot system includes a controller that is configured to actuate the motor drive to move the cervical seal responsive to the signals of the contact from the contact sensor. Variations of the system include a contact sensor that is either a pressure sensor, capacitance sensor, impedance sensor, and optical sensor. Alternatively, the contact sensor can include multiple contact sensors, including combinations of those listed above.

In some aspects, the techniques described herein relate to a method of treating tissue in a patient's uterine cavity, including: providing a medical robot system with robotic arm having a plurality of moveable arm segments with a distal arm segment carrying a plurality of motor drives for moving at least one device coupled to the distal arm segment; a resecting device detachably coupled to the distal arm segment, the resecting device having an elongate shaft extending about longitudinal axis to a working end carrying a cutter configured to rotate and/or axially reciprocate; introducing the working end of the resecting device transcervically into the patient's uterine cavity; actuating the resecting device to rotate and/or reciprocate the cutter; and utilizing a controller operates at least one of the plurality of motor drives to move the working end of the resecting device in a predetermined pattern to resect tissue.

The methods disclosed herein can further include a controller that operates a motor drive to move the working end in an axial pattern while actuating the cutter to resect tissue. In addition, the controller can operate a motor drive to move the working end in a rotational pattern while actuating the cutter to resect tissue.

The present disclosure is related to commonly assigned U.S. patent application Ser. No. 17/662,182, the entirety of which is incorporated by reference.

BRIEF DESCRIPTION OF DRAWINGS

Additional aspects of the invention will become clear from the following description of illustrative embodiments and from the attached drawings, in which:

FIG. 16C illustrates another subsequent step of the method where the robotic arm is actuated to advance the resection device through the working channel of the endoscope into the uterine cavity, and further actuating the robotic arm to angle the working end of tubular cutter towards a targeted fibroid, and also showing a cervical seal advanced to contact the cervix.

FIG. 16D illustrates another subsequent step of the method with the robotic arm moving the working end of the tubular cutter laterally further to resect the fibroid.

DETAILED DESCRIPTION

Figure 1:
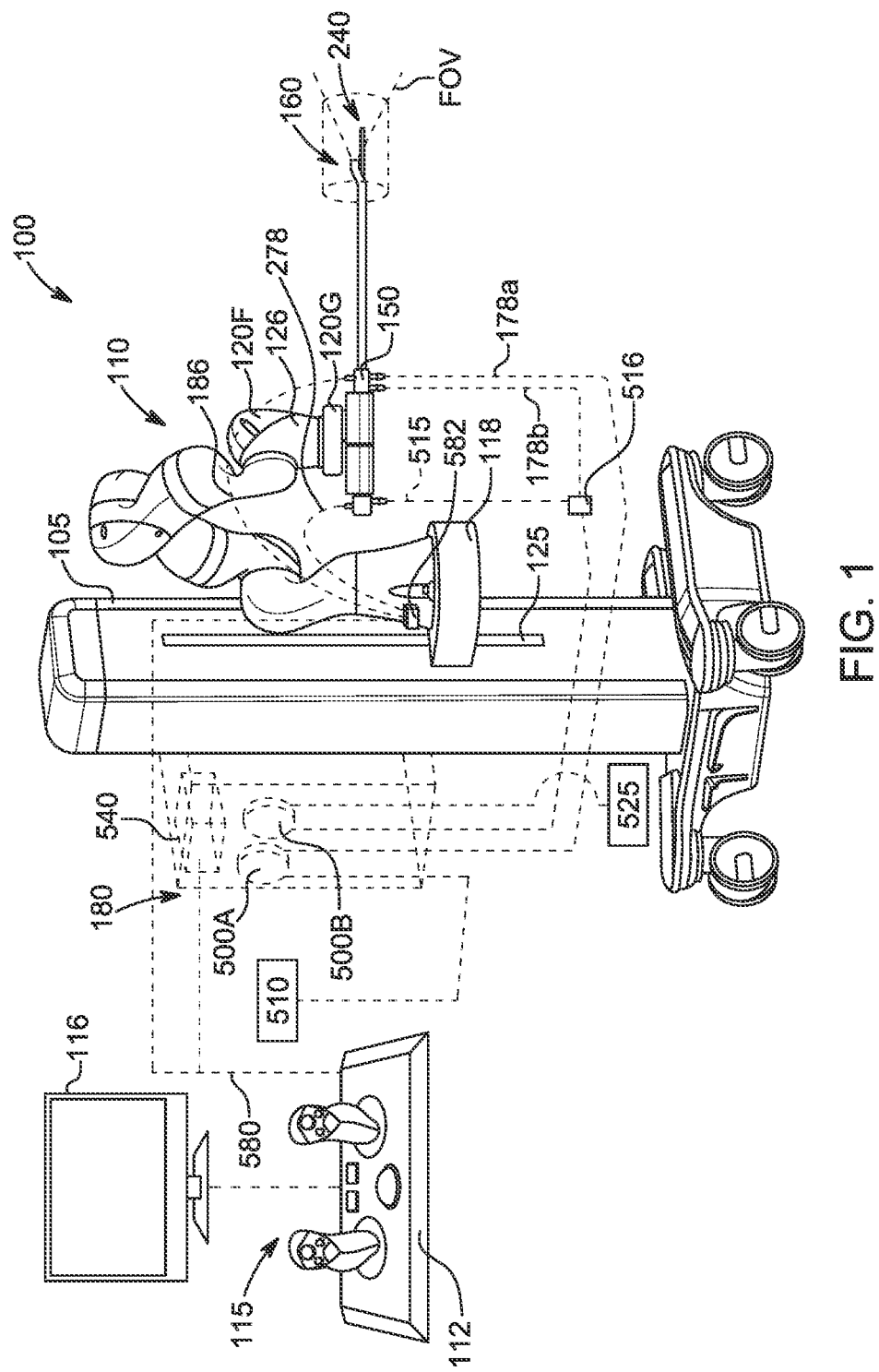
FIG. 1 is an illustration of a surgical robotic system, including a roll stand with a tower portion, a surgical console, and user input interface, and a surgical robotic arm adapted to carry and robotically manipulate multiple tools in procedures to treat intrauterine tissues.

FIG. 1 illustrates a surgical robotic system 100 adapted for use in gynecology procedures or other procedures with similar access requirements that includes a roll stand 104 with a vertical column or tower 105 that carries a surgical robot assembly comprising a robotic arm 110 that is operated from a console 112 with user input interface 115 and image display 116. The user input interface 115 can comprise one or more joysticks, rollerballs, and other input mechanisms known in the art. The image display 116 may be a touch screen that can further be used to direct movement of the arm 110 and/or control other operating parameters of the system 100 as described below. The robotic arm 100 is capable of movement relative to multiple axes as provided by multiple drives and actuators. In one variation, a robotic arm 110 of the system 100 can comprise as a core unit a commercially available, multiple-segment robotic arm manufactured by KUKA Robotics Corporation, having an office at 51870 Shelby Parkway, Shelby Township, Mich., 48315.

Figure 2:
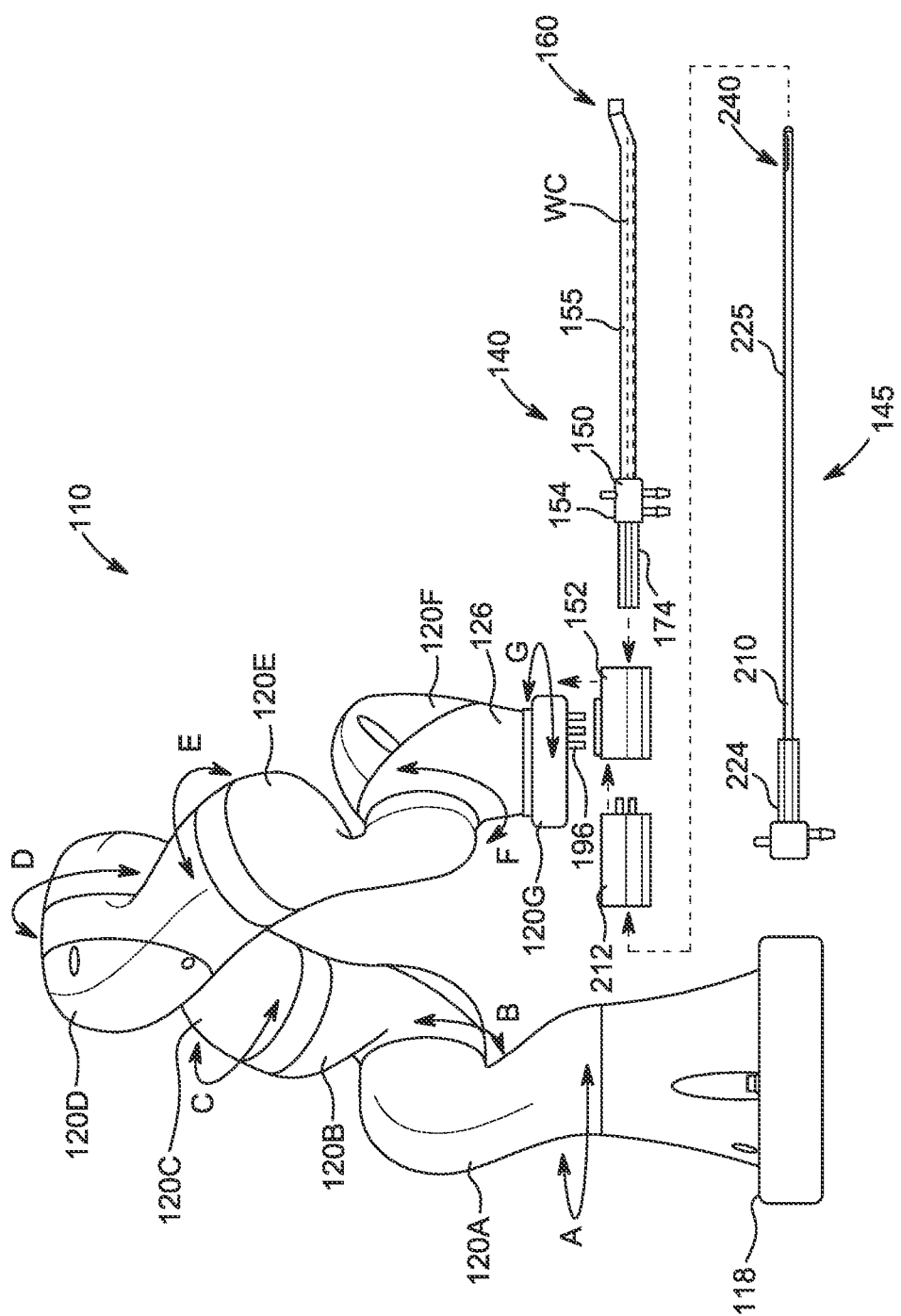
FIG. 2 is an enlarged view of the robot arm of FIG. 1 with a single-use endoscopic viewing system and a single-use tissue resecting device detached from the robotic arm.
Figure 3:
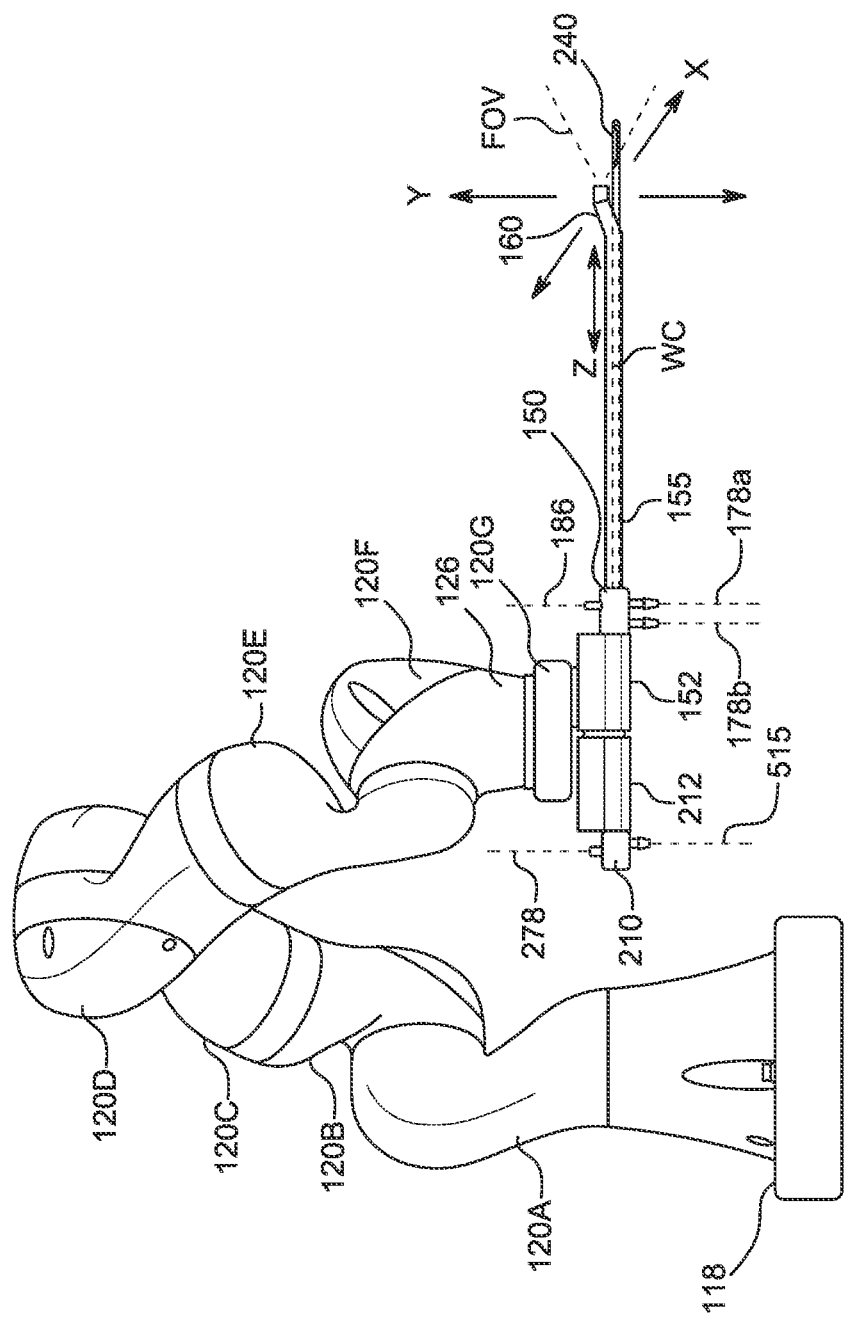
FIG. 3 is a view similar to FIG. 2, with the endoscopic viewing system and tissue resecting device locked into place in the robotic arm.

Referring to FIGS. 1 and 2, the lower base platform 118 of robotic arm 110 is motor driven to move vertically on a vertical rail 125 within the tower 105 of the roll stand 104. In a variation, the robotic arm 110 is configured with seven moveable arm segments 120A-120G, with the base rotational arm segment 120A rotating relative to base platform 118 (FIG. 2). The arm segments 120A-120G are adapted to rotate as indicated by arrows A through G in FIG. 2. The distal end 126 of the sixth arm segment 120F is coupled to the seventh rotating segment 120G that is motor driven to rotate. As will be described below, additional motor drives and surgical tools are adapted for detachable coupling to rotating arm segment 120G. Referring to FIG. 3, in a surgical procedure, it can be understood that the robotic arm 110 can move the distal end of a tool in all directions, angles, pitch, and yaw, for example, directions X, Y, and Z.

Referring to FIGS. 2 and 3, it can be seen that the first and second cooperating tools are adapted for attachment to the rotating segment 120G. The first tool is a single-use endoscopic viewing assembly 140 and the second tool is a single-use tissue resecting device 145 configured for insertion through a working channel WC in the endoscopic viewing assembly 140. In FIG. 2, the endoscopic assembly 140 and the resecting device 145 are shown detached from the rotating segment 120G of the robotic arm. In FIG. 3, the endoscopic assembly 140 and the resecting device 145 are fully assembled with the robotic arm 110.

Figure 4:
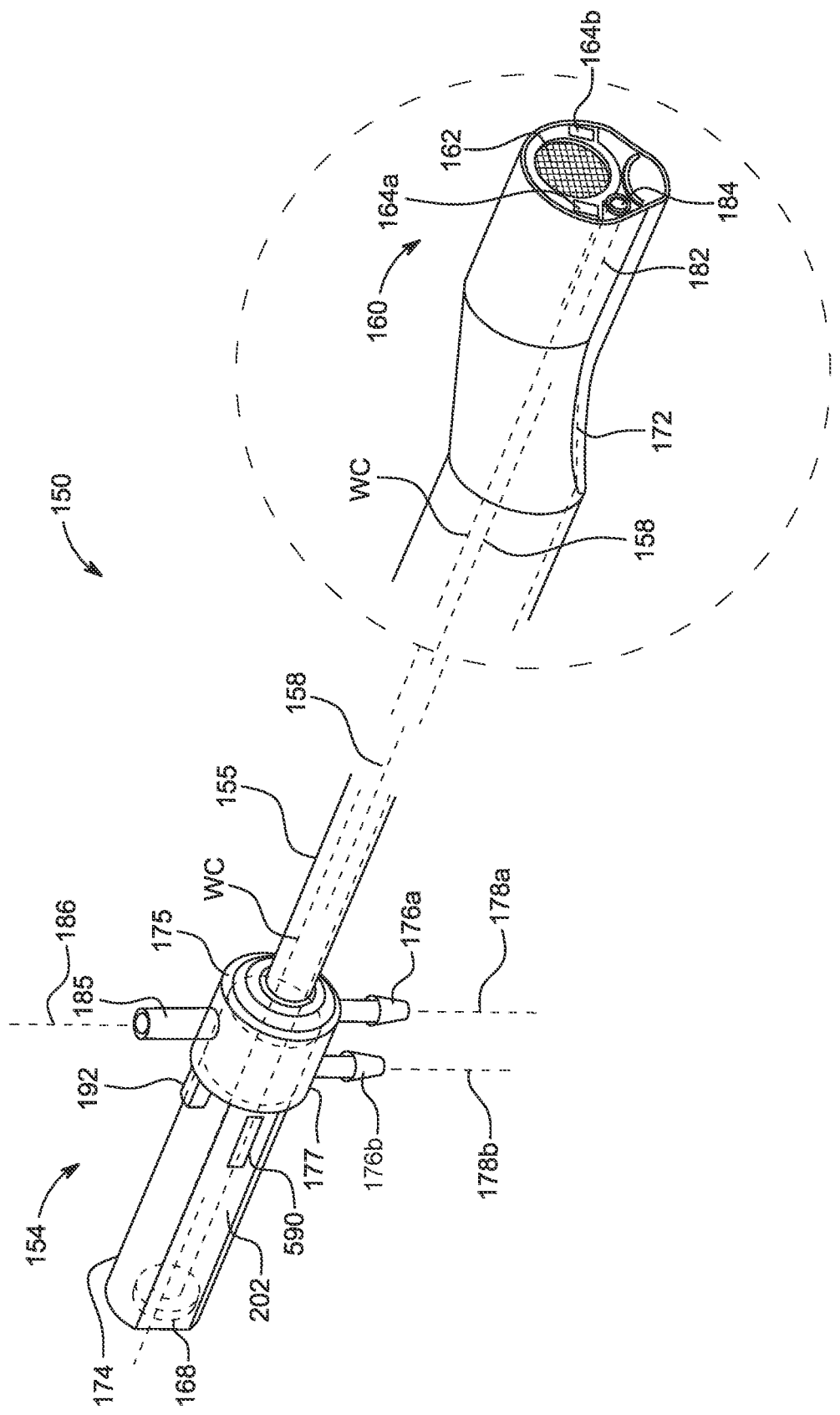
FIG. 4 is a perspective view of the proximal housing and the working end of the single-use endoscope of the endoscopic viewing system of FIGS. 1-3, wherein the endoscope is of the type that has an expandable and collapsible working channel in its working end.
Figure 5:
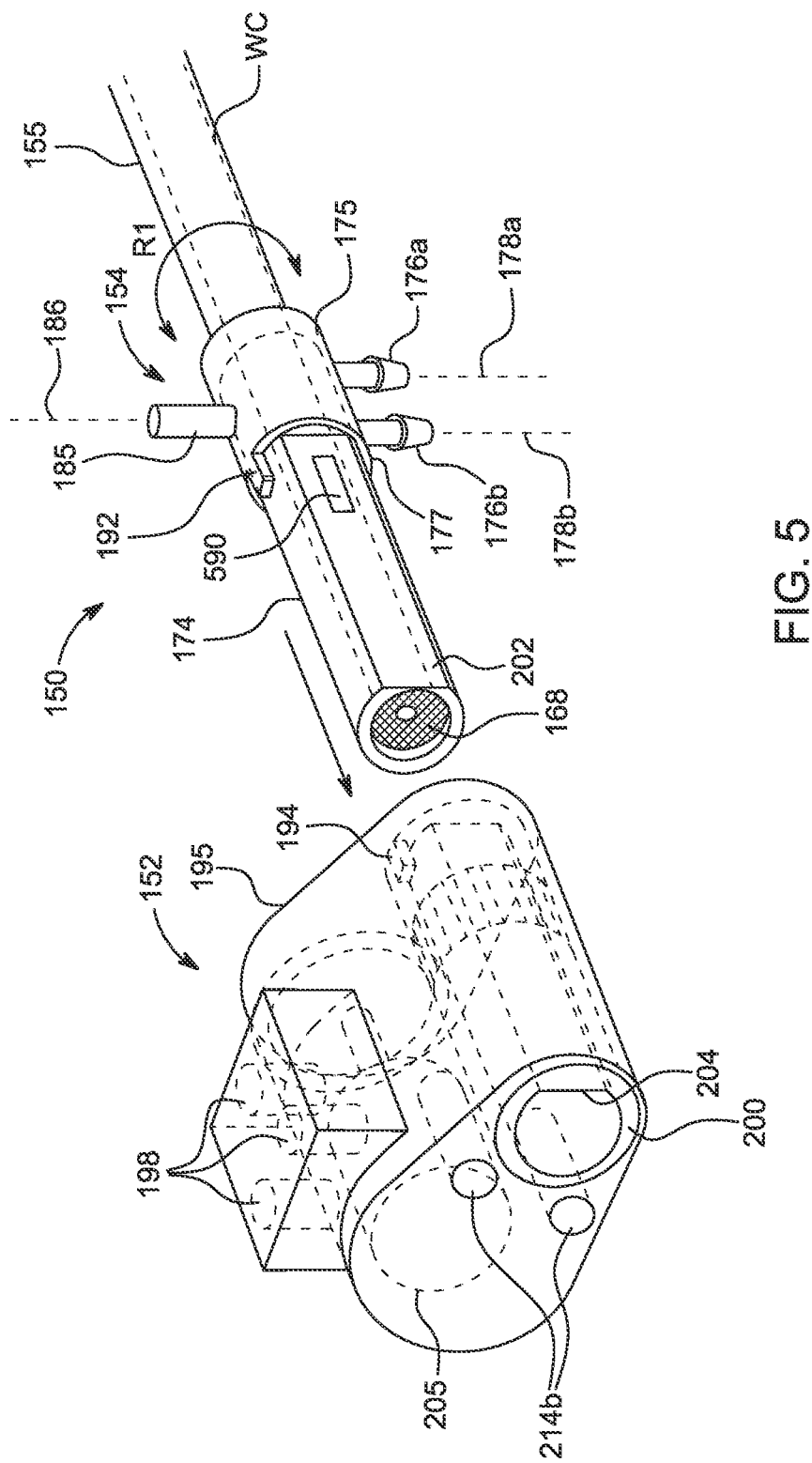
FIG. 5 is a perspective view of the endoscopic viewing system of FIGS. 1-3 from a different angle of the proximal housing and the working end of the single-use endoscope, which has an expandable and collapsible working channel.

FIGS. 4 and 5 are enlarged illustrations of the endoscopic viewing assembly 140 that comprises an endoscope 150 (FIG. 4) and an endoscope drive component 152 (FIG. 5). The endoscope 150 has a proximal hub 154 coupled to an elongated shaft 155 extending about a longitudinal axis 158 to a working end 160 that carries an image sensor 162 and at least one LED with two LEDs 164a and 164b shown in this variation (FIG. 4). The endoscope 150 has a working channel WC with a proximal seal 168, wherein the working channel extends through the elongated shaft 155 to the working end 160 of the endoscope. In FIG. 4, it can be seen that the working end 160 of the endoscope has an S-shape or curve in a repose or insertion shape with a small cross-section that allows for atraumatic introduction through a patient's cervical canal. The working channel WC has a distal region 172 that is expandable in cross-section to receive the shaft of a component of the resecting device 145, shown in FIG. 6, or to receive the shaft of any similar tool with a straight, rigid shaft. The working end 160 of the endoscope shaft 155 of FIG. 5 and other related endoscopes with expandable working channels and systems are described in more detail in commonly-owned U.S. Pat. Nos. 10,433,717 and 11,259,695 and commonly-owned U.S. patent application Ser. Nos. 15/975,626; 16/351,909; 16/562,069; 16/848,050; 17/447,380 and 17/490,643 which are incorporated herein by this reference.

Referring to FIGS. 4 and 5, it can be seen that the hub 154 of the endoscope 150 has a proximal extending portion 174 and a rotating collar 175 that carries two Luer fittings 176a and 176b in its inferior surface 177. Luer fitting 176a is adapted for coupling to the fluid inflow tubing 178a from a tubing set of a fluid management system 180 shown in FIG. 1 and described further below. The second Luer fitting 176b is adapted for coupling to outflow tubing 178b the fluid management system 180 (FIG. 1). The inflow tubing 178a communicates with an inflow channel 182 in the endoscope shaft 155 with an open termination 184 in the working end 170 (FIG. 4). The working channel WC in the endoscope shaft 155 functions as the fluid outflow channel and communicates with Luer fitting 176b and outflow tubing 178b. The arrangement of components in the interior of rotating collar 175 that allow for inflows and outflows from the rotatable endoscope shaft 155 to the rotating collar 175 is described in more detail in commonly-owned U.S. Pat. No. 10,433,717, which is incorporated herein by reference.

The superior surface of the rotating collar 175 includes a connector 185 for connecting an electrical cable 186 to the endoscope 150 to carry signals from the image sensor 162 to an image processor and to carry electrical current to LEDs 164a-164b. The rotating collar 175 includes a projecting key 192 that projects into a receiving notch 194 in the housing 195 of the drive component 152, which is adapted to maintain the rotating collar 175 in an upright position during use as the endoscope shaft 155 is rotated (see FIG. 5). The upright position of the collar 175 is useful for maintaining the inflow and outflow tubing 178a, 178b, and the electrical cable 186 (FIG. 1) in upright, non-rotating positions as the endoscope shaft 155 is rotated.

Now turning to FIG. 5, the endoscope drive component 152 may be adapted for single-use or multiple-use and typically would be adapted for multiple uses. In a variation, the drive component 152 detachably couples to arm segment 120G with pins 196 that are mated with bores 198 in the housing 195 of the drive component 152 (see FIG. 2).

Referring again to FIG. 5, the endoscope drive component 152 carries a rotating receiver 200 adapted to receive the proximal extending portion 174 of hub 154 of the endoscope 150. FIG. 5 shows that the proximal extending portion 174 has a keyed surface 202 that cooperates with keyed surface 204 of the rotating receiver 200, which provides for rotational locking of the endoscope 150 and drive component 152. The rotating receiver 200 is operatively coupled by a suitable gear mechanism to a motor drive 205 carried in the drive housing 195, and that is adapted to rotate the rotating receiver 200 and the endoscope 150 when locked in place in the direction of the arrow R1 in FIGS. 5 and 6. The motor drive 205 can be a DC stepper motor or other motor type and is adapted to rotate the rotating receiver 200 and locked-in place endoscope 150 from 180 o to 360 o. The gear mechanism can be any form of conventional straight gears that convert the motor shaft rotation to rotation of the receiver 200.

Figure 7:
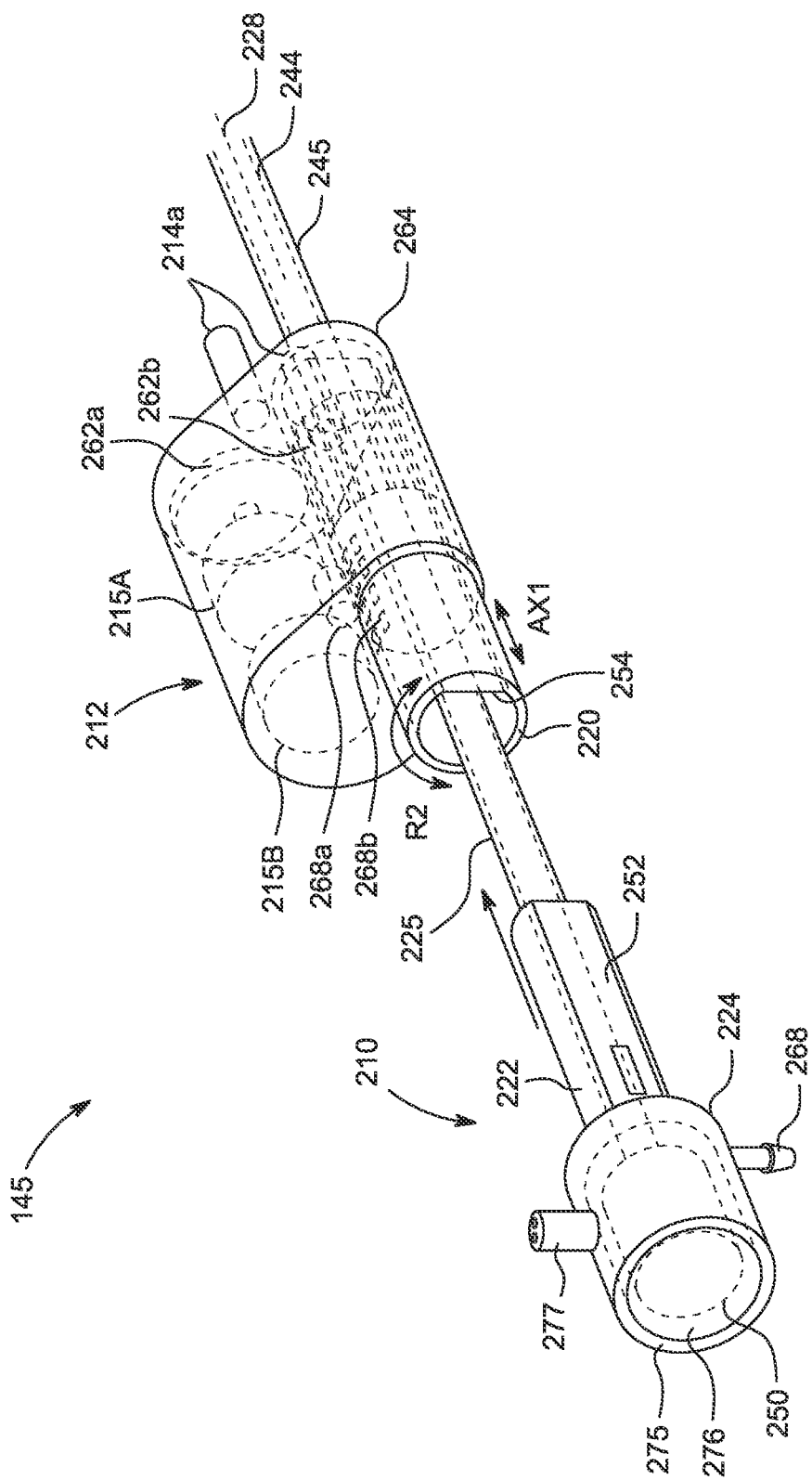
FIG. 7 is a perspective view of the proximal portion of a resection device that comprises a drive component and tubular cutter, where only the proximal housing of the tubular cutter is shown.
Figure 8:
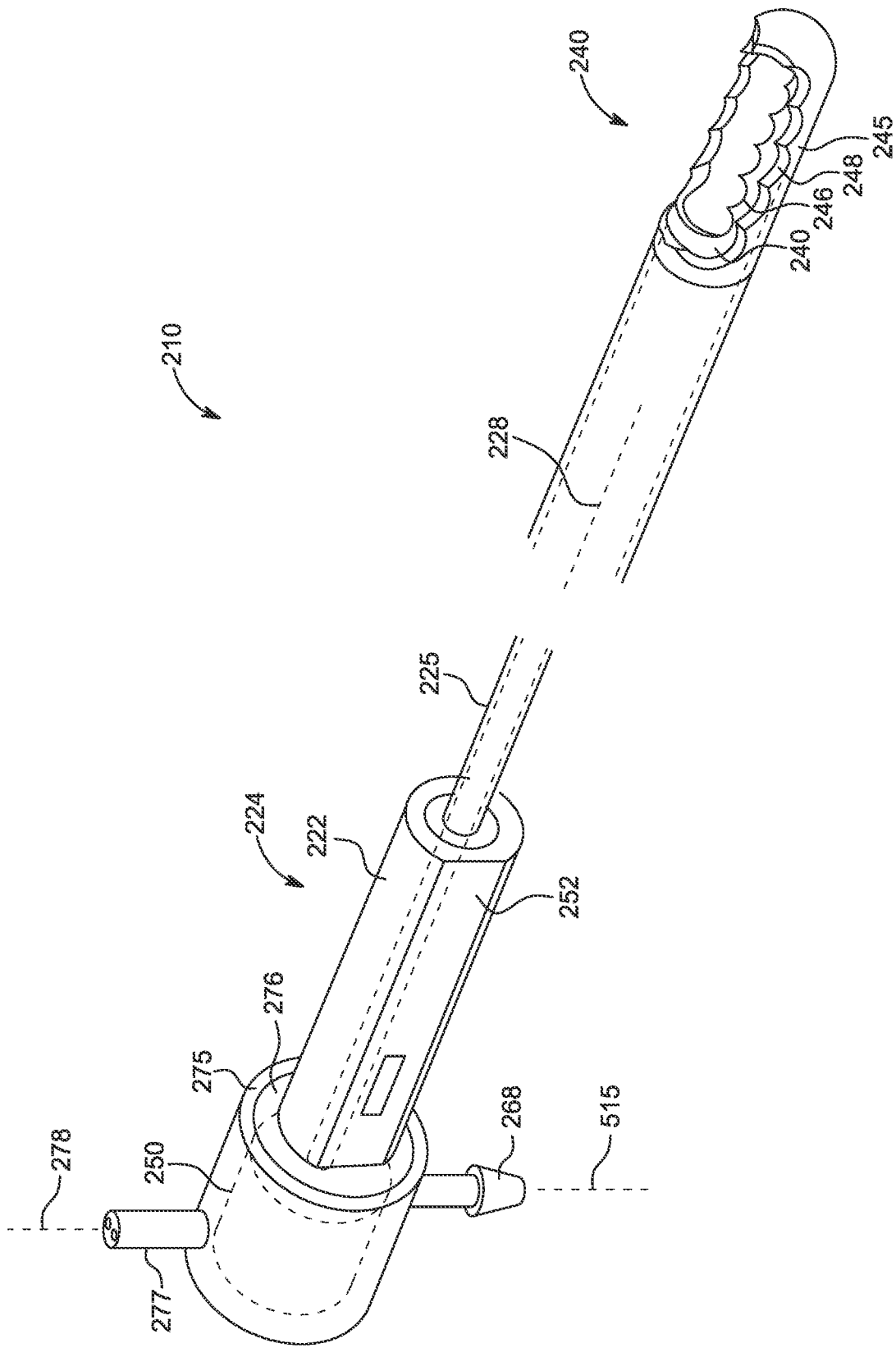
FIG. 8 is a perspective view of the tubular cutter of FIG. 7 with an enlarged view of the working end showing the rotating inner sleeve and cutting windows.

Now turning to FIGS. 7 and 8, the resection device 145 is illustrated and comprises a motor-driven tubular cutter 210 and a tool drive component 212. The drive component 212 may be adapted for single-use or multiple-use, and typically would be adapted for multiple uses. In a variation, the tool drive component 212 detachably couples to housing 195 of the endoscope drive component with pins 214a that are mated with bores 214b in the endoscope drive housing 195 (FIG. 5). The tool drive component 212 carries first and second DC motors 215A and 215B for respectively (i) rotating and (ii) axially moving a moveable receiver 220 in the drive component 212 that receives an extending portion 222 of the proximal housing 224 of the tubular cutter 210.

Figure 6:
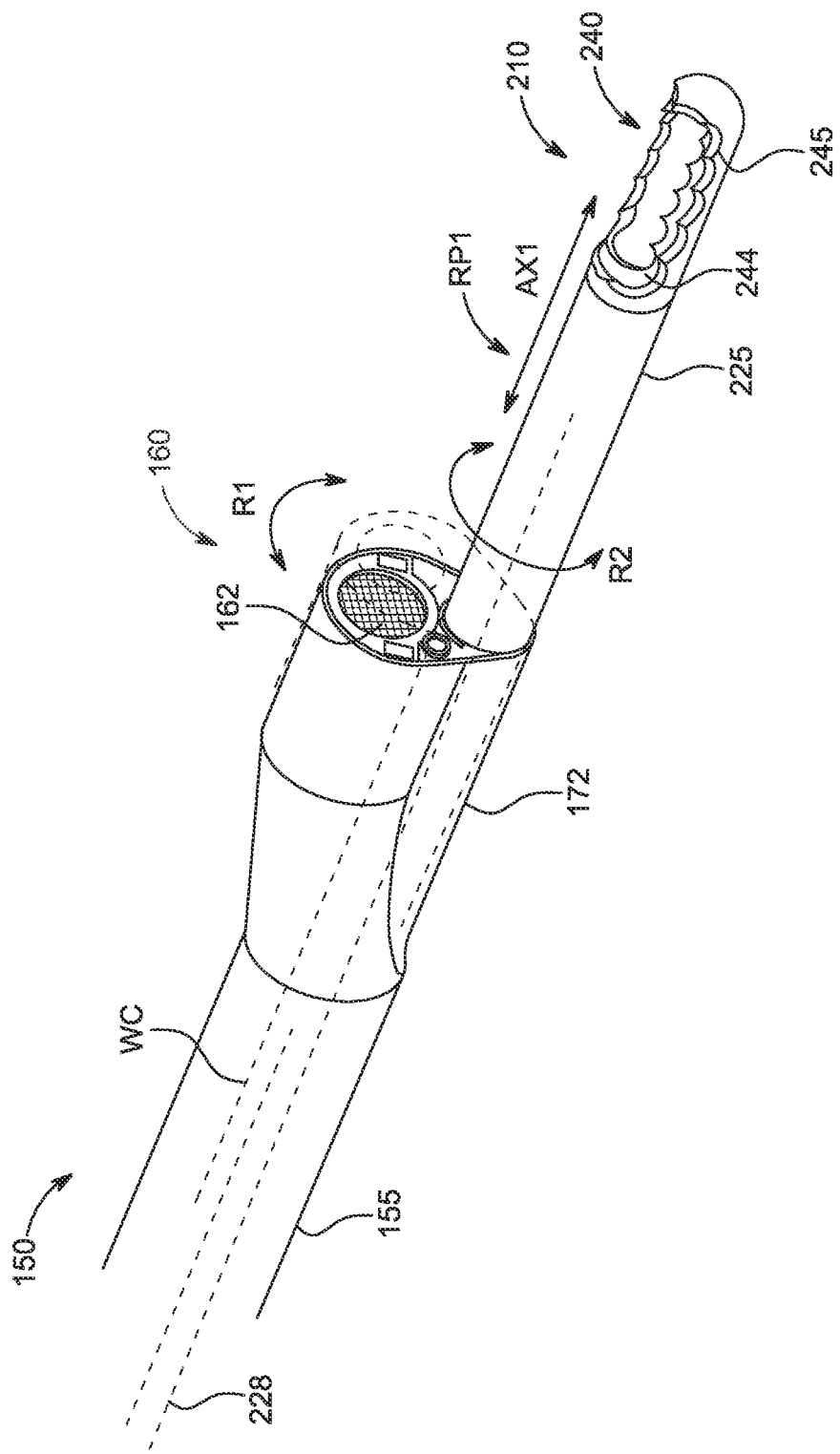
FIG. 6 is a perspective view of the working end of the endoscope of FIG. 4 with the shaft of a tubular cutter device inserted through the expandable-collapsible working channel of the endoscope and further showing a pre-selected or programmed robotic cutting pattern.

As can be seen in FIG. 6, shaft 225 of the tubular cutter 210 is adapted for introduction through the working channel WC of the endoscope shaft 155 of FIGS. 4 and 5. It should be appreciated that other treatment tools can be used other than a tubular cutter, such as any type of ablation or coagulation device, RF device, biopsy device, ultrasound device, laser device, dissector, retractor, or manipulator, with the tubular cutter 210 shown for purposes of illustration.

Referring to FIGS. 7 and 8, the tubular cutter 210 has a proximal housing 224 coupled to the elongated shaft assembly 225 that extends about axis 228 to a working end 240 adapted for tissue resection (FIG. 8). In FIG. 8, it can be seen that shaft assembly 225 comprises concentric inner and outer sleeves 244 and 245, respectively, where the inner sleeve 244 has an inner cutting window 246 that rotates in an outer cutting window 248 of the outer sleeve 245 to resect tissue (see FIG. 8). The proximal housing 224 of the tubular cutter 210 carries a motor drive 250 for rotating the inner sleeve 244 and inner cutting window 246 at a suitable rotational speed ranging from 1,000 RPM to 10,000 RPM or more for cutting tissue.

Now referring to FIG. 7, the tubular cutter 210 is shown partially inserted into the tool drive component 212. The rotating receiver 220 of the drive component 212 is adapted to receive the extending portion 222 of the proximal housing 224 of the tubular cutter 210. FIG. 7 shows that the extending portion 222 of the housing 224 has a keyed surface 252 that cooperates with a keyed surface 254 of the rotating receiver 220 to provide for a locked-in rotational engagement of the proximal housing 224 and receiver 220. As can be understood, the shaft 225 of the tubular cutter 210, when assembled with other components as in FIG. 1-3 is further introduced through the seal 168 into the working channel WC of the endoscope 150.

In a variation, the rotating receiver 220 in FIG. 7 is operatively coupled to the first motor drive 215A by a gear mechanism that rotates the moveable receiver 220, for example, with geared surfaces 262a and 262b. The first motor drive, 215A, is adapted to rotate the receiver 220 and engaged cutter 210 from 180 o to 360 o. As indicated by arrow R2 in FIGS. 6 and 7. The tool drive component 212 further carries the second motor drive 215B that is geared to move the receiver 220 axially in the housing 264 of the drive component 212. A suitable gear mechanism can consist of a worm gear 268a that engages features 268b in the surface of the receiver 220. Thus, the second motor drive 215B is adapted to axially move the rotating receiver 220 (and engaged tubular cutter 210) back and forth in the drive housing 212 in the direction of arrow AX1 when the tubular cutter 210 is locked in place. The motor drives 215A, and 215B again can be DC stepper motors or other suitable motor types. As can be understood, the second motor drive 215B is adapted to move the working end 240 of the tubular cutter 210 axially between a fully retracted position in the working channel WC of the endoscope 150 and a range of extended positions of the working end 240 as shown in FIG. 3 within the field of view FOV of the endoscope image sensor 162 during a procedure. The range of extension of the working end 240 beyond the endoscope 150 is up to 15 cm beyond the plane of the lens of the image sensor 162.

Referring to FIGS. 7 and 8, it also can be seen that the tubular cutter 210 is configured for use with the fluid management system 180. The fluid outflow tubing 178b of the fluid management system 180 is coupled to the Luer fitting 268 on the housing 224 of the tubular cutter 210. Fluid outflows and resected tissue is aspirated through the lumen of the inner sleeve 244 of the tubular cutter 210, as is known in the art. In FIGS. 7 and 8, it can be further seen that the proximal housing 224 of the tubular cutter 210 has a rotatable surface portion 275 that can freely rotate around a core portion 276. The arrangement of components in the interior of proximal housing 224 that allow for outflows from the tubular cutter 210 to communicate with the Luer fitting 268 in the rotatable surface portion 275 is described in more detail in commonly-owned U.S. Pat. No. 10,433, 717, which is incorporated herein by reference. The rotatable surface portion 275 also carries a connector 277 for coupling with an electrical cable 278 to carry current to the motor 250 in the tubular cutter 210. The upright position of the rotatable surface portion 275 is useful for maintaining the outflow tubing 178b and the electrical cable 278 (FIG. 1) in stable, non-rotating positions.

Figure 9:
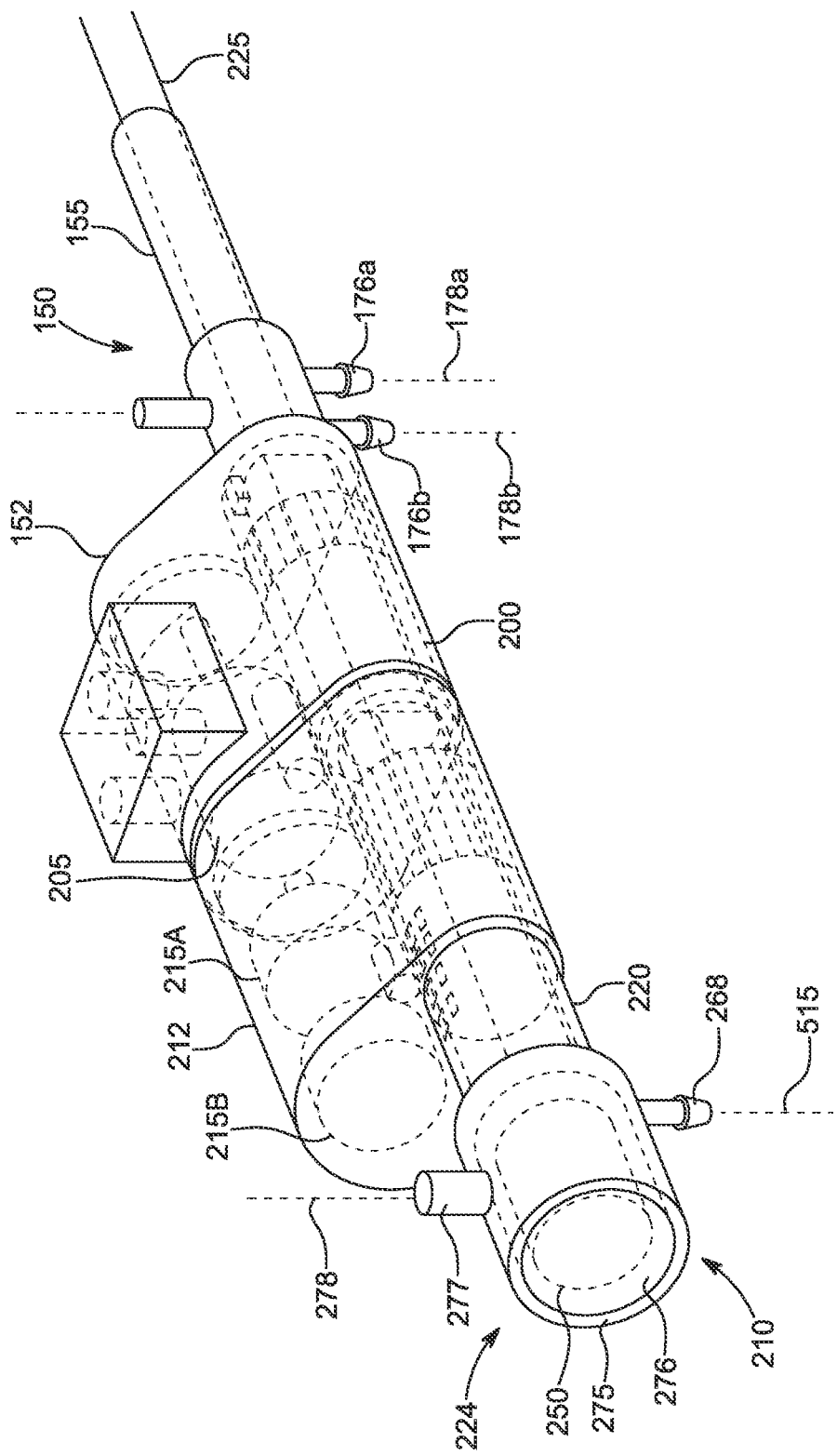
FIG. 9 is a perspective view of the proximal portions of the endoscopic viewing system and the resection device assembled as when detachably coupled to the robotic arm as in FIGS. 1 and 3.

Now turning to FIG. 9, it can be seen how the endoscopic viewing assembly 140 and the resecting device 145 can be assembled and coupled to the rotating robotic arm segment 120G. The first drive component 152 is lifted vertically to couple to the pins 196 in the arm segment 120G. Thereafter, the extending portion 174 of the endoscope's proximal hub 154 is inserted into the receiver 200 of the endoscope drive component 152. Next, the tool drive component 212 and its pins 214a are mated with the receiving bores 214b in the endoscope drive housing 195. Finally, the elongated shaft 225 of the tubular cutter 210 is introduced through both drive components 152, 212, and the working channel WC of the endoscope 150. FIGS. 1 and 3 illustrate the shaft 225 and working end 240 of the tubular cutter 210, both fully extended beyond the working end 160 of the endoscope 150, as an example. However, it should be appreciated that when using the robotic arm 110, the endoscope shaft 155 is initially introduced through the patient's cervical canal CC (FIGS. 16A-16B) with the working end 240 of the tubular cutter 210 retracted within the working channel WC of the endoscope 150 as shown in FIGS. 15A-15B.

Figure 10:
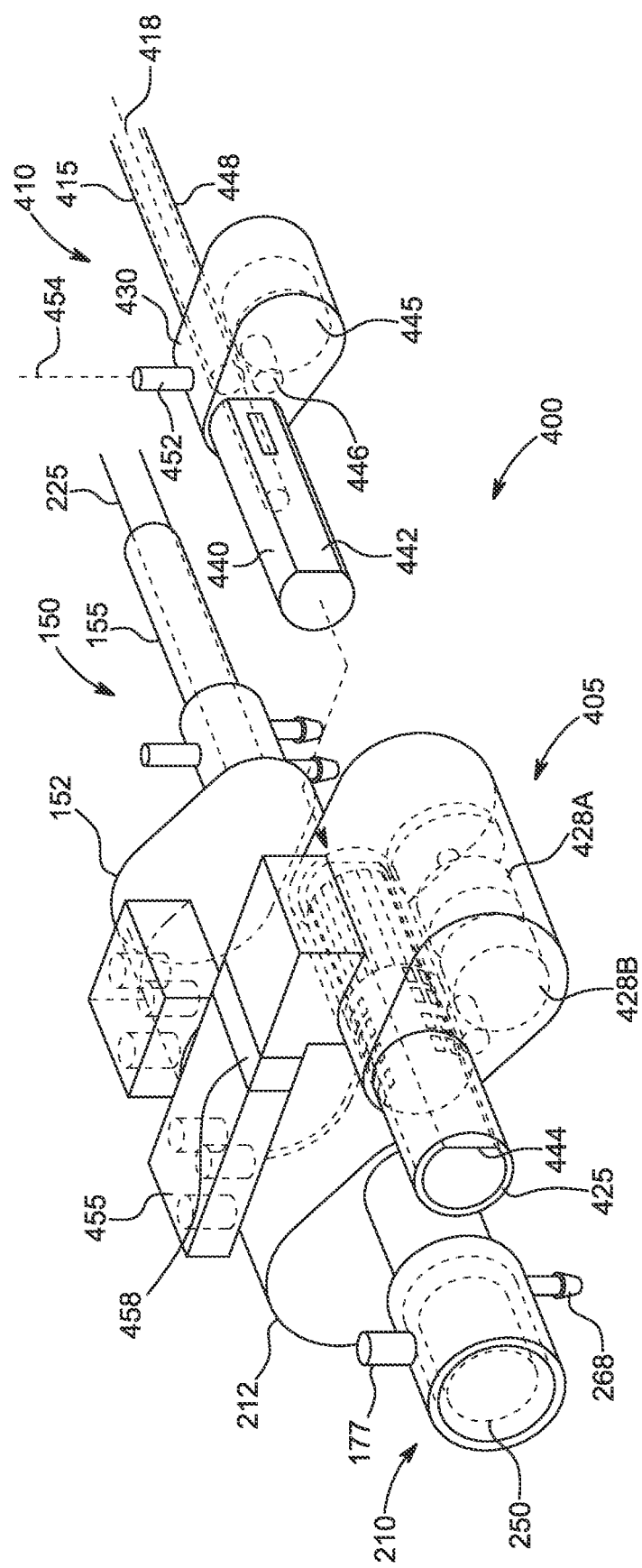
FIG. 10 is a perspective view of the proximal portion of a robotic tissue-stabilizing assembly with its drive component adjacent to the endoscopic viewing system and resection device of FIG. 9.
Figure 11:
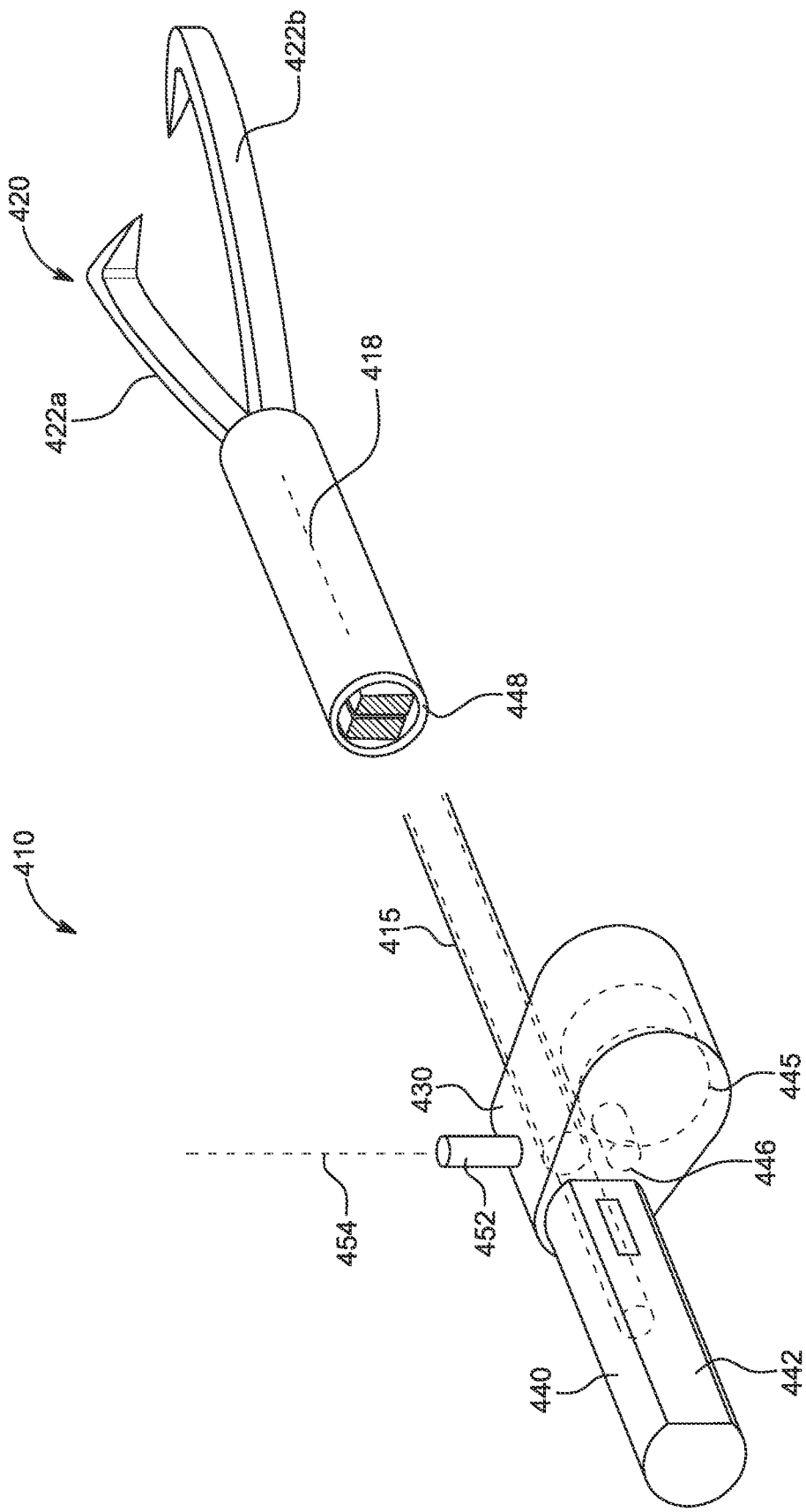
FIG. 11 is a perspective view of a tenaculum component of the tissue-stabilizing assembly of FIG. 10.
Figure 16B:
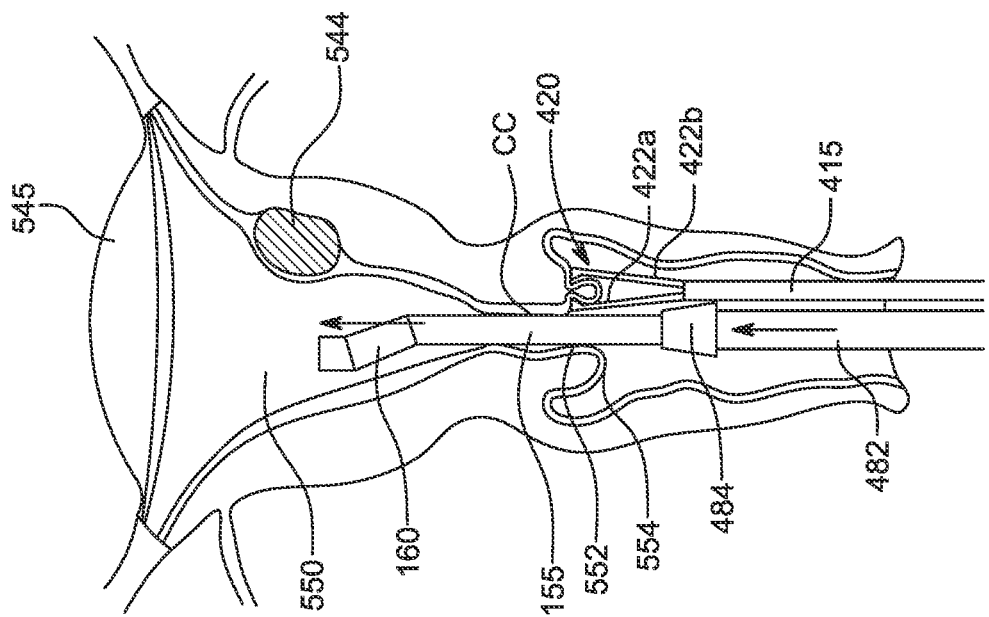
FIG. 16B is a schematic view of a subsequent step of the method illustrating the actuation of the robotic arm to advance the endoscope working end through the endocervical canal into the uterine cavity and also the movement of a cervical seal toward the patient's cervix.
Figure 16A:
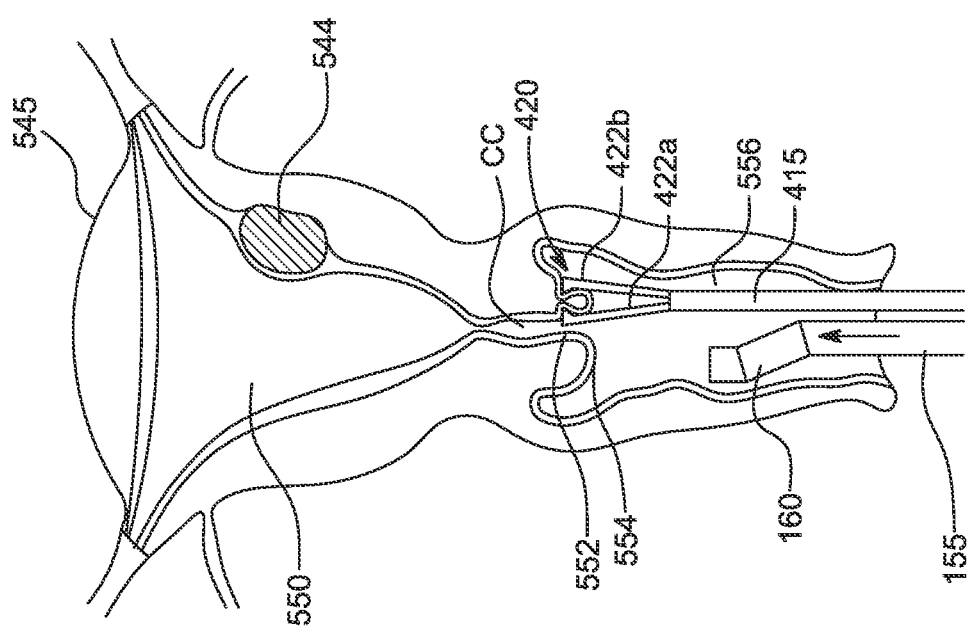
FIG. 16A is a schematic sectional view of a patient's uterus showing a step in a method of using the robotic arm to move a tenaculum-type into position to grasp the patient's cervix and move an endoscope toward the patient's cervix.

Now turning to FIGS. 10 and 11, another robotic component configured for use with the system 100 of FIG. 1, is shown that comprises a tissue-stabilizing assembly 400 adapted for engaging and gripping the patient's cervix as is known in the art. In any typical intrauterine procedure using a transcervical approach, the physician uses a tenaculum or forceps to grip and stabilize the patient's cervix to facilitate introduction of an endoscope shaft through the patient's cervical canal CC (FIGS. 16A-16B). In this robotic variation, the approach is similar, with the stabilizing assembly 400 being a robotic assembly. FIG. 10 shows the proximal portions of the endoscopic viewing assembly 140 and resecting device 145, together with the tissue stabilizing assembly 400. The tissue stabilizing assembly 400 again has a drive component 405 that is motorized to drive a tool or tenaculum component 410, shown more fully in FIG. 11. The tenaculum component 410 has an elongate shaft 415 extending about axis 418 to a working end 420 with openable-closeable first and second jaws 422a and 422b (FIG. 11). While FIGS. 10-11 illustrate a working end 420 in the form of a conventional tenaculum, it should be appreciated suction-contact working ends and other forms of graspers may be used to engage and stabilize a patient's cervix. In the variation shown, the stabilizer drive component 405 is similar to the previously described tool drive component 212 of FIG. 7 in that it again provides two motor drives for both rotational and axial movement of a receiver 425 therein that receives the tenaculum component.

As can be seen in FIG. 10, the drive component 405 carries first and second motors 428A and 428B that are configured to move the receiver 425 both rotationally and axially. The drive systems can be the same as those described in the tool drive component 212. The proximal handle or housing 430 of the tenaculum 410 again includes an extending portion 440 with a keyed surface 442 that cooperates with the keyed surface 444 in the receiver 425. The tenaculum component 410 further carries a motor drive 445 with a suitable gear mechanism such as a worm gear 446 for advancing and retracting the outer sleeve 448 of the shaft assembly 415 as indicated in FIG. 11 to close and open the jaws 422a and 422b. The proximal housing 430 also carries a connector 452 for connecting an electrical cable 454 to the housing 430 to deliver current to the motor 445. In FIG. 10, it can be seen that stabilizer drive component 405 has a bracket 455 for coupling the tissue-stabilizing assembly 400 to the robotic arm 110, for example, with a multiple pin arrangement of the type described previously. In one variation shown in FIG. 10, a middle portion of the bracket 455 of the stabilizer drive component 405 can include a flexible or resilient material 458 to allow for flexing between that stabilizer drive component 405 and the other tools.

Figure 12:
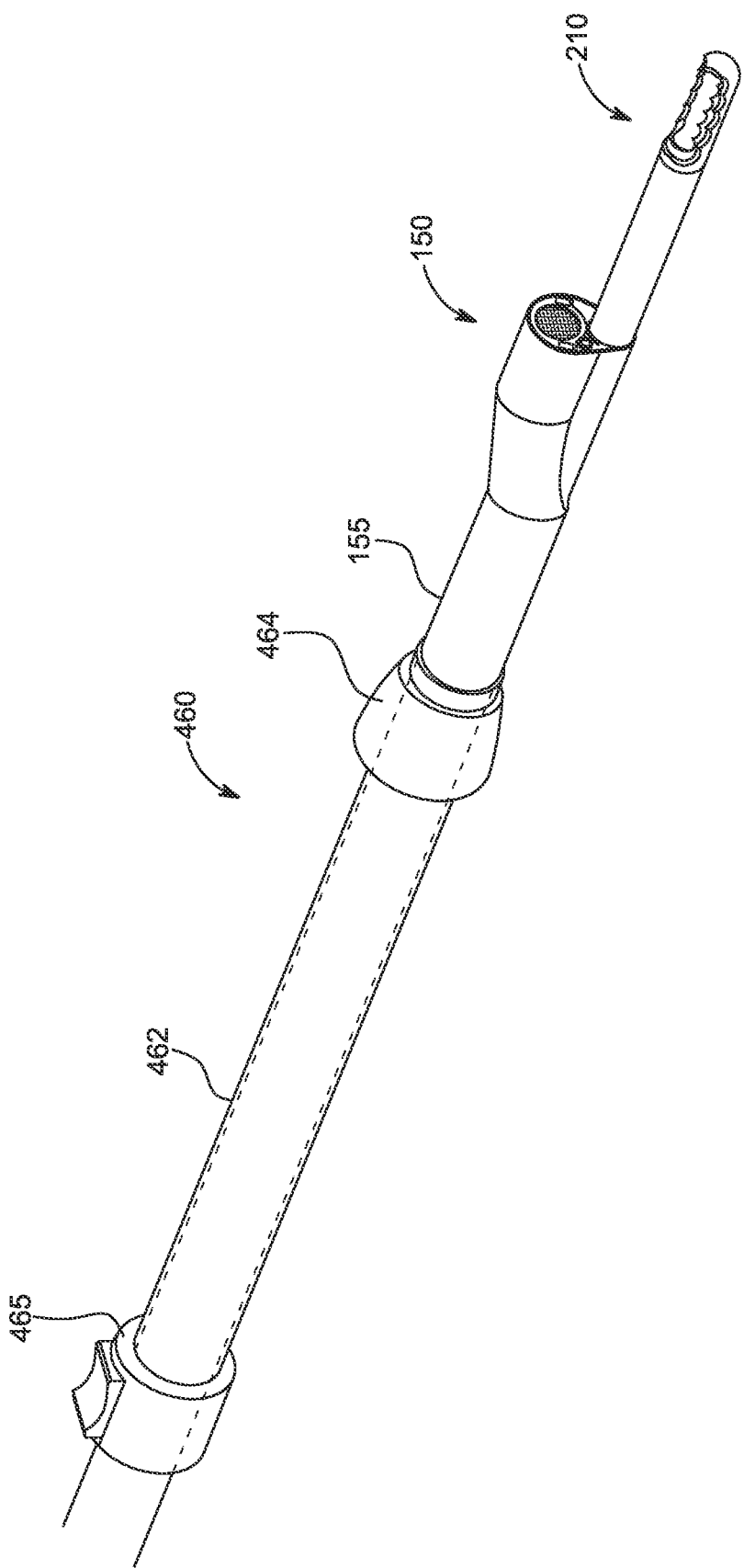
FIG. 12 is a perspective view of a cervical seal component that is slidably mounted over the shaft of the endoscope.

FIG. 12 shows another component of the invention which comprises a cervical seal 460. Such a cervical seal 460 comprises a concentric sleeve 462 that slides over the shaft 155 of the endoscope 150. The cervical seal 460 carries a tapered distal seal member 464 that can be pushed against the patient's cervix CC and optionally into the cervical canal CC to prevent distention fluid from escaping the uterine cavity through the cervical canal (see FIG. 16B). In this variation, the cervical seal 460 is mounted on the endoscope shaft 155 during manufacturing and is manually moved axially with a locking mechanism 465 at a proximal end of the sleeve 462.

Figure 13:
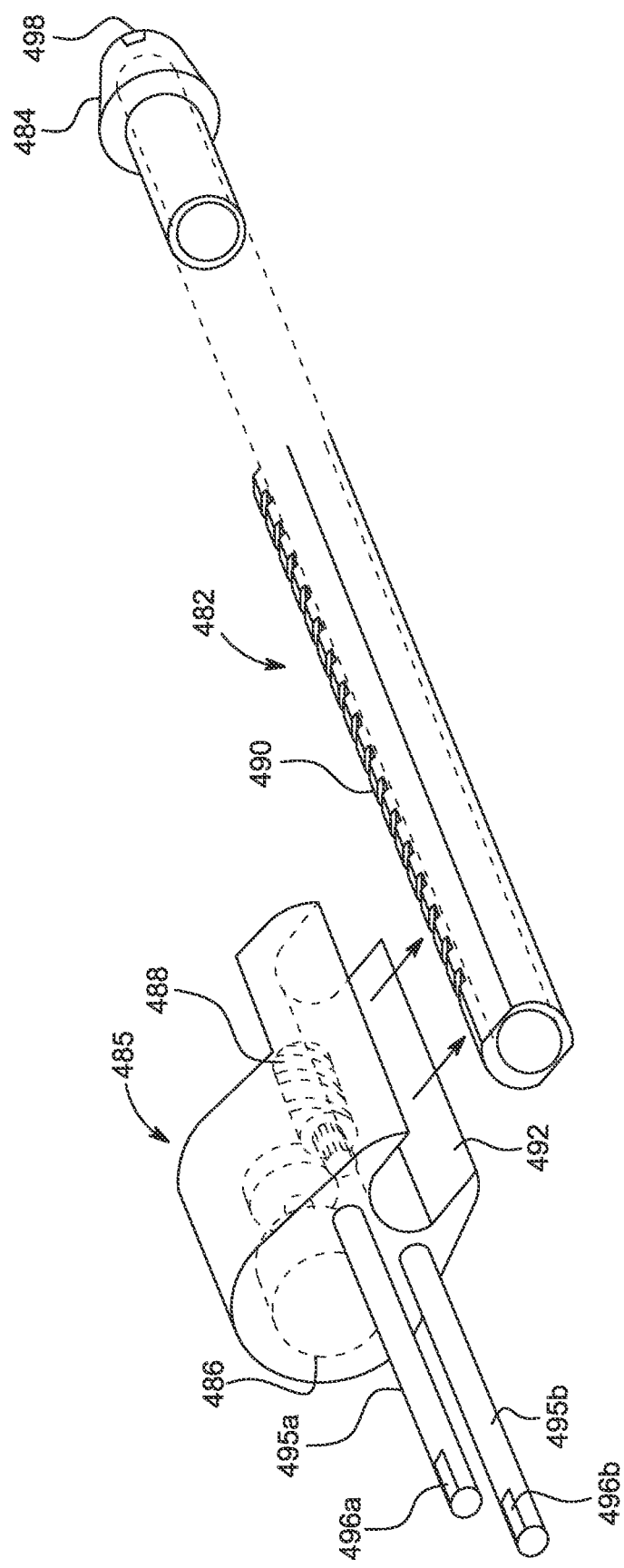
FIG. 13 is a perspective view of a robotically operated cervical seal assembly that is slidably mounted over the shaft of the endoscope.
Figure 14:
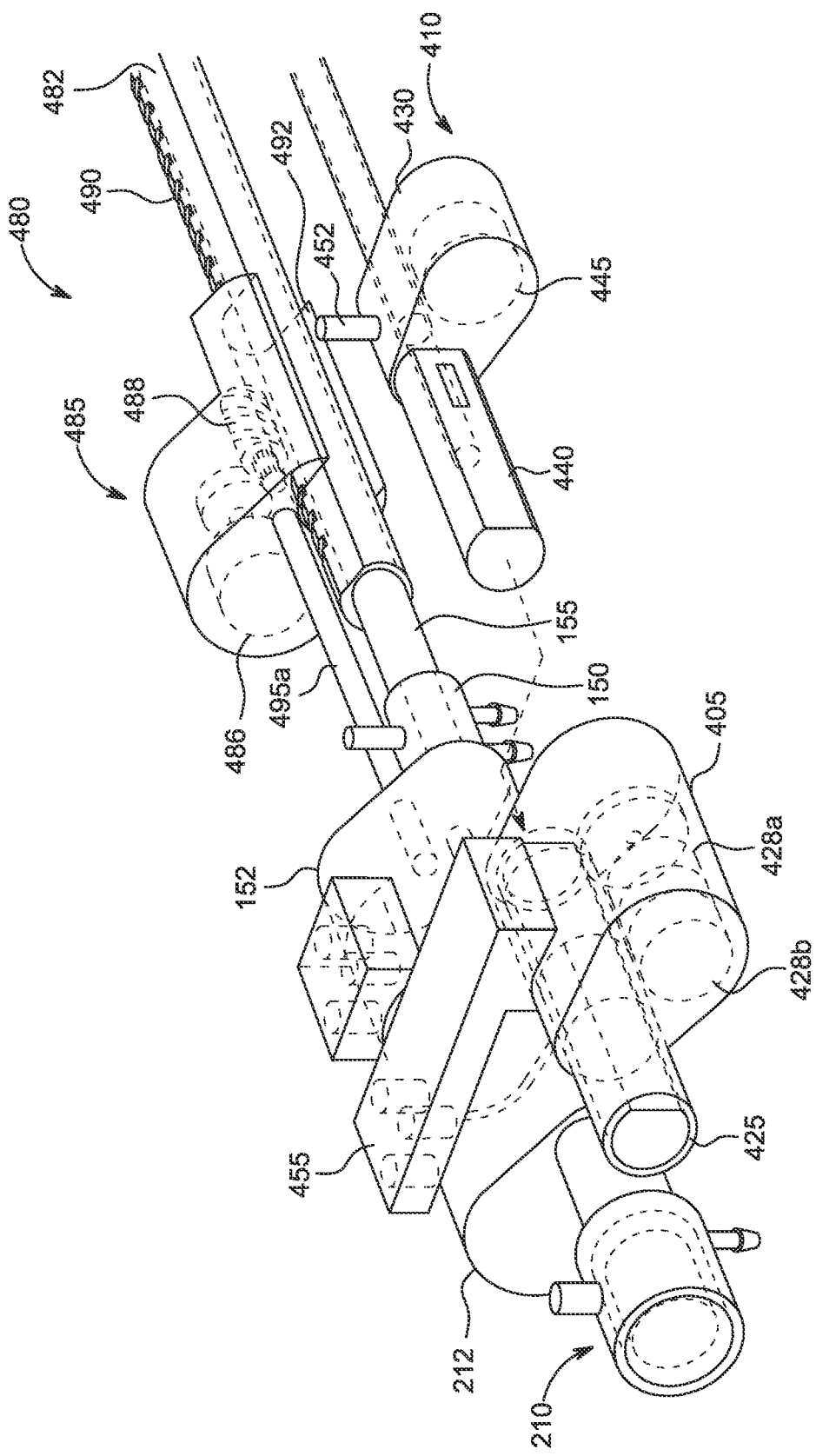
FIG. 14 is a perspective view of the proximal portion of the robotic cervical seal assembly of FIG. 13, shown assembled with the tissue-stabilizing assembly, endoscopic viewing system, and resection device of FIG. 10.

Now turning to FIGS. 13 and 14, a robotically controlled cervical seal 480 is shown that again comprises a sleeve 482 that extends over the endoscope shaft 155 with a distal tapered seal member 484 that contacts the patient's cervix. In this variation, referring to FIG. 14, a seal drive component 485 is provided that is adapted to robotically and automatically move the seal sleeve 482 back and forth to maintain a proper seal. Similar to the other drive components described above, the seal drive component 485 unit has a DC motor 486 that drives a worm gear 488 that engages projecting features 490 on the sleeve 482 to move the sleeve back and forth. In this variation, the drive component 485 has an open-sided slot 492 for receiving the sleeve 482 so that the drive can be mounted over the already assembled endoscope 150 and its drive component 212. In one method of use, the cervical seal sleeve 482 would be advanced manually to engage the cervix, and then the drive component 485 would be positioned in place to engage the seal sleeve 482 for continuous adjustment during a resection procedure using a sensor system described below. The cervical seal sleeve 482 may need an extended range of motion, and the robotic adjustment is best suited for precise shorter axial movements once the seal member 484 is proximate to the patient's cervix. In FIGS. 13-14, it can be seen that the seal drive component 485 has elongated mounting pins 495a and 495b that are adapted to couple the housing 195 of the endoscope drive component 212, as shown in FIG. 14. In this variation, the mounting pins 495a and 495b carry electrical contacts 496a and 496b for engaging cooperating electrical contacts in the endoscope drive housing 195 to carry current to the DC motor 486 in the seal drive component 485.

In one variation, the cervical seal 480 can have one or more sensors 498, as shown in FIG. 13, for sensing contact with the patient cervix, which send signals to a controller 500 to operate the drive component 485 to move and maintain the seal member 484 in suitable engagement with patient's cervix to prevent leakage of distention fluid. Such a sensor 498 can be any suitable sensor with a wired connection through the electrical contacts 496a and 496b or a wireless connection to the controller 540 or controllers, such as a capacitance sensor, impedance sensor, pressure sensor, light sensor, or the like.

Figure 15:
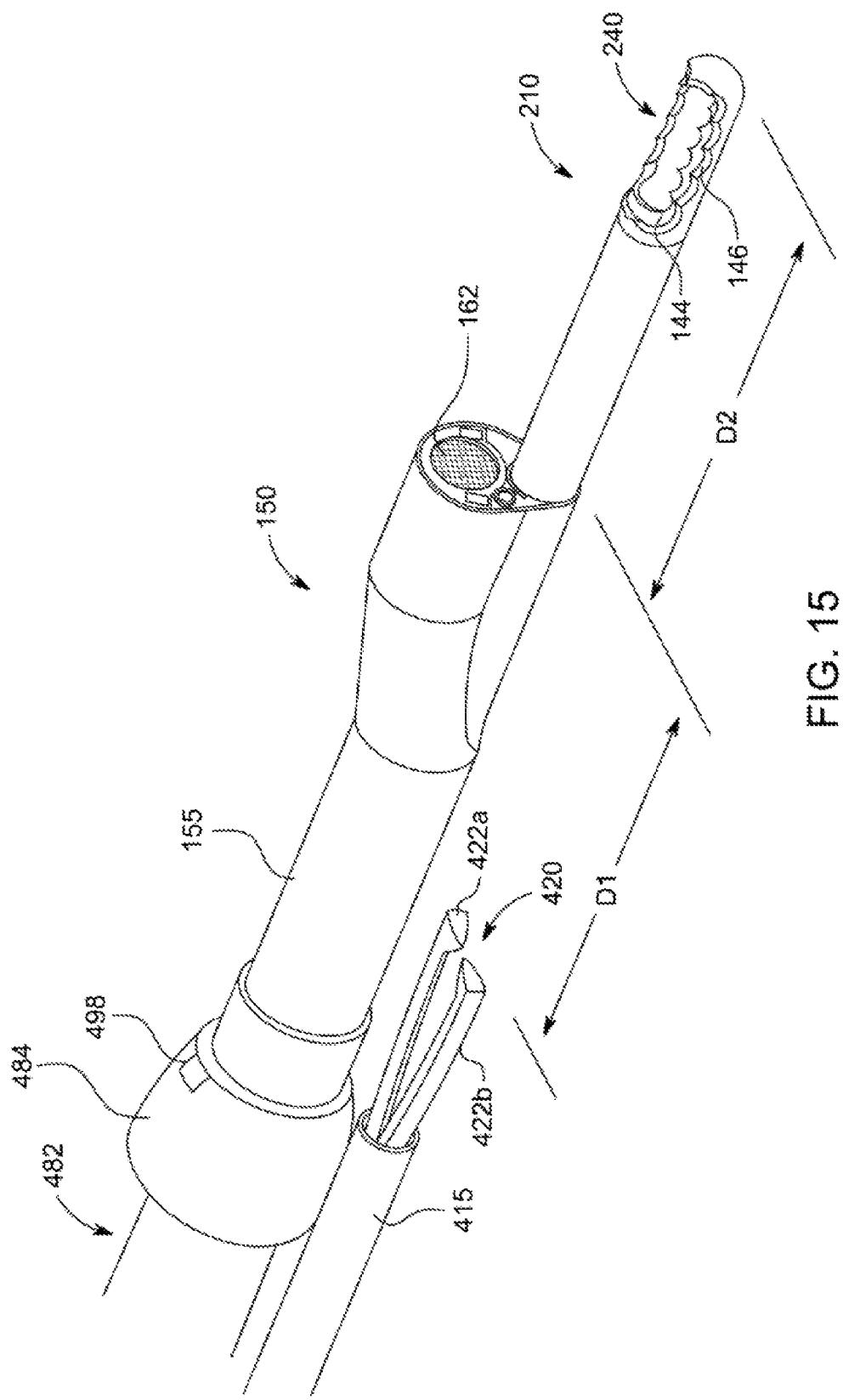
FIG. 15 is a perspective view of the distal working ends of the endoscope, the cervical seal, the tubular cutter, and the tenaculum, indicating the dimension of robotic movements of some of the components.

FIG. 14 illustrates the four robotically driven components (endoscopic viewing assembly 140, resecting device 145, tissue-stabilizing assembly 400, cervical seal 480), and the steps of assembling the three components can be understood. In use, as will be described below, the illustrations of the receivers of the drive components may not be drawn to scale, and it can be appreciated that the extendable dimensions of the tools relative to one another may be substantial. FIG. 15 illustrates the working ends of the devices, and it can be understood that the tenaculum shaft 415 initially is configured to be extendable beyond the endoscope working end 160 by up 10 cm to grip the patient's cervix (FIG. 16A). Thereafter, the endoscope shaft 155 is introduced through the patient's cervical canal CC while the clamped tenaculum working end 420 remains stationary so that drive component 152 is configured to extend the endoscope working end 160 a distance D1 in FIG. 15 that is up to 15 cm beyond the tenaculum working end 420 (FIG. 16B). Further, the tool drive component 212 and tubular cutter 210 are configured to extend the working end 240 of the tubular cutter a distance D2 in FIG. 15 that is up to 10 cm beyond the end of the working channel WC and image sensor 162 (FIG. 16C). Also, the cervical seal member 484 requires a large range of axial adjustments over the endoscope shaft 155, where both manual and robotic adjustments are used as described above.

Referring back to FIG. 1, the fluid management system 180 is operatively connected to the endoscope 150 and tubular cutter 210, as is known in the art. The fluid management system 180 includes an inflow peristaltic pump 500A and an outflow peristaltic pump 500B. Inflow tubing 176a has a proximal end coupled to a fluid source 510, such as a saline bag with the distal end of the inflow tubing 178a connected to the Luer fitting 176a in an inferior surface of the endoscope handle 154. The inflow pump 500A is adapted to provide a fluid flow through inflow tubing 178a and a flow channel 182 in the endoscope shaft 155 to an outlet 184 in the working end 160 of the endoscope (see FIG. 4). In a variation, the outflow tubing 178b is coupled to Luer fitting 176b on the endoscope 150 (FIG. 4), and a branch 515 of the outflow tubing 178b is coupled to the Luer fitting 268 on the tubular cutter 210 (FIG. 5). A valve or flow diverter 516 may be provided in outflow tubing 178b to select an outflow fluid path from the endoscope 150 or the tubular cutter 210 (FIGS. 1 and 3). The fluid management system 180 thus allows use of the endoscope 150 alone where inflows and outflows are through the endoscope shaft 155 when no cutting device occupies the working channel WC of the endoscope 150. When the tubular cutter 210 is positioned in the working channel WC as shown in FIG. 3, the outflows would flow through the tubular cutter 210 and fitting 268 on its handle 224. The outflow pump 500B thus is adapted to cause fluid flows from a working space to a collection reservoir 525. A tissue trap (not shown) may be provided in the outflow tubing 178b. Independent motor drives are provided to operate the first and second peristaltic pumps 500A and 500B and are controlled by controller 540 or controllers (FIG. 1), which typically are configured to maintain a set pressure in a working space such as a uterine cavity.

Now turning to FIGS. 16A to 16D, a method of the invention in using the robotic system 100 and the various tools is shown in schematic views in a robotic procedure to resect a fibroid 544 in a patient's uterus 545. The fibroid 544 is shown in a wall of the uterine cavity 550, but it should be appreciated that in other variations of methods, the targeted tissue can be polyps, adhesions, endometrium, and other abnormal tissues as well as fibroids or myomas. In FIG. 16A, it can be understood that the user has actuated various segments of robotic arm 110 to align the endoscope shaft 155 and tenaculum shaft 415 with the external os 552 of the patient's cervix 554 after being advanced into the patient's vagina 556, which may be held open with a suitable speculum device (not shown). FIG. 16A shows that under endoscopic vision, the endoscope 155 and tenaculum jaws 422a and 422b are robotically manipulated axially and rotationally as needed and then closed to grasp the cervix 554 to thereby stabilize the cervix.

FIG. 16B illustrates a subsequent step of the method wherein the user operates the robotic arm 110 to advance the endoscope working end 160 in its reduced cross-section or insertion profile through the cervical canal CC into the uterine cavity 550. The fluid management system 180 is typically actuated to provide fluid inflows through the endoscope 150 to facilitate introduction of the working end 160 through the cervical canal CC. The S-shaped end of the endoscope working end 160 may be rotated to position it optimally relative to the tenaculum jaws for introduction into the cervical canal CC. FIG. 16B further illustrates the step of manually advancing the seal sleeve 482 and seal member 484 toward the cervix 554 and cervical canal CC.

FIG. 16C illustrates the seal sleeve 482 and seal member 484 fully advanced to contact the cervix 554, either manually or with drive member 485, to prevent distension fluid from leaking outwardly from the cervical canal CC. FIG. 16B further shows the user actuating the tool drive component 212 to advance the shaft 225 of the tubular cutter 210 through the working channel WC in the endoscope shaft 155 into the uterine cavity 550, which expands the distal portion of the working channel WC as described above. FIG. 16C further shows the robotic arm 110 be actuated to move the distal ends 160 of the endoscope 150 and the distal end 240 of the tubular cutter 210 in the direction or plane X to interface with the surface of the fibroid 544.

FIG. 16D illustrates the user operating the robotic arm 110 further to tilt the working end 240 and cutting windows of the tubular cutter 210 into the fibroid 544 to resect and remove tissue. It should be understood that this step of the method of resecting tissue can include moving the working end 240 of the cutter 210 axially and/or rotating the working end slightly back and forth to resect the fibroid 544. Further, the user may rotate the shaft 155 of the endoscope to reposition the image sensor 162 and LED's, as shown in FIG. 6, to acquire the best view of the surface of the fibroid 544 that is being resected. During the resection procedure, the seal drive component 485 can operate to adjust the seal 484 to maintain contact with the cervix to prevent fluid leakage, as described above.

While FIG. 16D illustrates the step of a method of resecting a fibroid, it should be further appreciated that operating parameters of the tubular cutter 210 and the robotic system 100 can be controlled or automated during the resection by the controller 540 or multiple controllers of the robotic system 100. In a variation, for example, the fluid management system 180 can be controlled by the user from the user input interface 115 during resection, which includes adjusting any operating parameter of the fluid management system. Operating parameters of the fluid management system include (i) adjusting the set pressure in the uterine cavity, (ii) increasing fluid inflow temporarily as a flush mechanism to clear resected debris or blood from the viewing field, (iii) increasing fluid pressure to a selected level for a selected time interval as a tamponade, and (iv) adjusting the fluid deficit level and any warnings or system shut-down associated with a fluid deficit. The user can also adjust operating parameters of the endoscope 150 from the user input interface 115, which include (i) adjusting light from the LEDs, and (ii) capturing images or videos of the procedure.

The user can also adjust operating parameters of the tubular cutter 210 at the user input interface 115, which includes (i) adjusting rotational speed of the inner cutting sleeve 144, and (ii), in some variations, adjusting oscillation and/or translation of the inner cutting sleeve 144 within the outer sleeve 146 during use. As is known in the art, tubular cutters may use rotating cutting sleeves, reciprocating cutting sleeves, or rotating and axially translating cutting sleeves.

Figure 17:
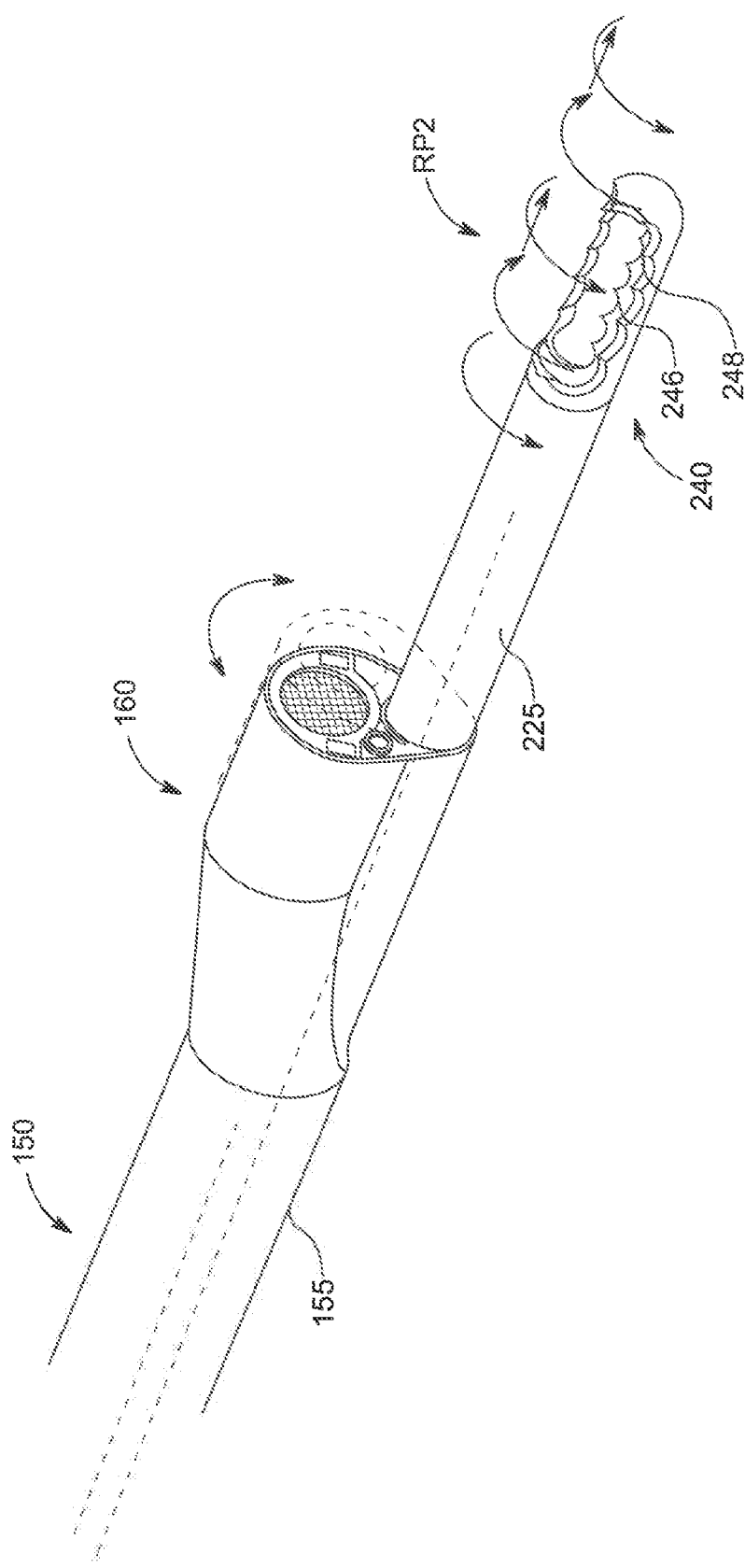
FIG. 17 is a perspective view of the working ends of the endoscope and the tubular cutter showing a pre-selected or programmed robotic cutting pattern.

In another variation of a method of resecting tissue, referring to FIG. 6 and FIG. 17, the controller 540 or controllers of the robotic system 100 can automate parameters of a resecting interval in a preset "resecting plan" in which actuation of drive components of the resecting device and the motors of the robotic arm 110 move the working end 160 of the tubular cutter 210 in preset movements while operating to efficiently resect tissue. For example, in FIG. 6, the user can select via user input interface 115 a resecting plan "RP1" in which the inner cutting sleeve 144 is operated at a selected RPM between 1,000 RPM and 10,000 RPM while contemporaneously the drive component 212 moves the working end 160 axially back and forth (direction AX1 in FIG. 6) at a selected rate from 0.1 cm/sec to 1.0 cm/sec and for a selected reciprocating distance of 0.1 cm to 2 cm. The resecting plan RP1 can operate for a preset number of seconds, for example, from 5 seconds to 30 seconds, or can be initiated and terminated by user input. Another preset resecting plan (not shown) can operate the inner cutting sleeve 244 at an RPM range described above while contemporaneously actuating the drive component 212 to rotate working and 160 of the tubular cutter 210 from 10 o to 180 o degrees at a selected rate ranging between 10 o/sec and 90 o/sec. Another variation can consist of a preset resecting plan "RP2," as shown in FIG. 17, which combines both reciprocation and rotation within the parameters described above to resect tissue for any pre-selected time interval or by initiation and termination by the user. FIG. 17 depicts discrete, sequential axial and rotational movements, but a zig-zag movement is possible with contemporaneous axial and rotational movements. At the same time that the working end 160 of the tubular cutter 210 is being used in any preset resecting plan, the user can rotate the working end 160 of endoscope [144] 150 (FIGS. 6 and 17) to optimize the viewing of the resection of tissue. In any of the resecting plans above, the user would further operate the robotic arm to move the cutter working end 240 in any direction X, Y, or Z (FIG. 3. To optimally engage the targeted tissue.

In FIG. 1, it can be seen that the console 112 with user input interface 115 is connected by a cable 580 to a controller 540 and to a connector 582 at the base of the robotic arm 110. The various tools and drive units 140 and 145 also can connect by cables, for example, cables 186 and 278 to the connector 582 to provide for electrical power transmission and electrical signaling between all the tools, the console 112 and the controller 540 or controllers. While electrical cables are shown, it should be appreciated that electrical signaling also may be wireless.

In another variation, referring back to FIGS. 4 and 5, the extending portion 174 of the housing 154 of endoscope 150 that is received by the receiver 200 can carry one or more load sensors 590 or force sensors around the circumference of the housing that interface with the receiver 200 to sense forces being applied to the working ends 160, 225 240 and shafts 155, 225 of the endoscope 150 and tubular cutter [240] 210 during a resecting procedure (FIG. 16D). Signals from the force sensor(s) 590 are received by the controller 540, and a control algorithm can continuously monitor the forces and the direction of forces on the shafts 155 and 225 of the devices. In a variation, excess forces, such as bending forces, on the shafts 155 and 240 225 can provide an audible signal or a visual signal that forces are exceeding a preset level, or the control algorithm can stop operation of the resecting device or automatically initiate a movement of the robotic arm in a suitable direction to reduce forces on the shafts 155 and 240 225 of the endoscope 150 and the tubular cutter 240210. In another variation, any preset resecting plan above (e.g., RP1 of FIG. 6; RP2 of FIG. 17) can include a resection plan that actuates the robotic arm 110 to move the working end 240 of the cutter 210 in a pre-selected range of X, Y, and Z movements (see FIG. 3) wherein the force-sensing algorithm further automatically controls and maintains a pre-selected pressure on the working end 240 as it engages and resects tissue. It should be appreciated that such force sensors 590 can be positioned in any tool housing or any cooperating drive unit where the sensing forces on the tenaculum 410 also may be useful.

In general, a robotic system 100 of the invention comprises a surgical robotic arm 110 with a base and a plurality of arm segments that rotate or translate relative to a plurality of axes, wherein at least one distal segment of the robotic arm is adapted for detachably coupling to a single-use endoscopic viewing system 140, a resecting device 145 and a tissue-stabilizing system 400 that all can be operated with robotic drive mechanisms to move the tools from a remote user input interface 115.

A method of the invention for treating targeted tissue in a patient's uterine cavity comprises providing a robotic arm having a plurality of arm segments to provide movement of the robotic arm relative to a plurality of axes, wherein a distal arm segment carries a single-use endoscope with an elongate shaft having a working channel therein, wherein the endoscope shaft has a first insertion profile having a non-expanded shape and and a second expanded shape by introduction of a shaft of a treatment tool through the working channel, and thereafter (i) operating the robotic arm to introduce the endoscope shaft in its first insertion profile through the patients cervical canal into a uterine cavity, (ii) operating the robotic arm to introduce the shaft of the treatment tool through the working channel thereby expanding the working channel to its second expanded shape and moving the working end to its expanded working profile, and (iii) treating the targeted tissue in the uterine cavity with the working end of the treatment tool. Additionally, robotic stabilizing carried by the robotic arm ac be used to stabilize the patient's cervix before introducing the endoscope through the patient's cervical canal.

Although particular embodiments of the present invention have been described above in detail, it will be understood that this description is merely for purposes of illustration and the above description of the invention is not exhaustive. Specific features of the invention are shown in some drawings and not in others, and this is for convenience only, and any feature may be combined with another in accordance with the invention. A number of variations and alternatives will be apparent to one having ordinary skills in the art. Such alternatives and variations are intended to be included within the scope of the claims.

Particular features that are presented in dependent claims can be combined and fall within the scope of the invention.

The invention also encompasses embodiments as if dependent claims were alternatively written in a multiple dependent claim format with reference to other independent claims.

It is important to note that where possible, aspects of the various described embodiments or the embodiments themselves, can be combined. Where such combinations are intended to be within the scope of this disclosure. All references, including publications, patent applications, and patents, cited herein are hereby incorporated by reference to the same extent as if each reference were individually and specifically indicated to be incorporated by reference and were set forth in its entirety herein.

What is claimed is:

1. A medical robot system for use in intrauterine procedures, comprising:
   a robotic arm having a plurality of moveable arm segments;
   an endoscopic viewing assembly detachably coupled to a distal segment of the robotic arm, the endoscopic viewing assembly having an elongate endoscope shaft extending about a longitudinal axis to a distal end carrying an image sensor; and
   a stabilizing device detachably coupled to a distal segment of the robotic arm, the stabilizing device having an elongate tool shaft extending about a longitudinal axis adapted for engaging tissue to stabilize a cervix of a patient;
   a treatment tool detachably coupled to a distal segment of the robotic arm, the treatment tool having a treatment tool shaft extending about a longitudinal axis to a working end, wherein the treatment tool shaft is configured for introduction through a working channel of the endoscopic viewing assembly; and
   a motor drive configured to move the elongate tool shaft axially relative to its longitudinal axis, and where the motor drive is configured: to rotate the treatment tool shaft relative to its longitudinal axis, and to move the treatment tool shaft axially relative to its longitudinal axis.

2. The medical robot system according to claim 1 further comprising an endoscope motor drive configured to rotate the elongate endoscope shaft relative to its longitudinal axis.

3. The medical robot system according to claim 1 further comprising an endoscope motor drive configured to move the elongate endoscope shaft axially relative to its longitudinal axis.

4. The medical robot system according to claim 1 wherein the endoscopic viewing assembly carries a working channel extending therethrough.

5. The medical robot system according to claim 1 wherein the treatment tool comprises at least one of a resection device, ablation device, coagulation device, biopsy device and dissection device.

6. The medical robot system according to claim 1 wherein the treatment tool comprises a resection device with a moveable cutting member, and further comprising a resecting motor drive for moving the moveable cutting member moves at least rotationally or axially.

7. The medical robot system according to claim 1 further comprising a cervical canal sealing assembly coupled to at least one of the robotic arm and the endoscopic viewing assembly.

8. The medical robot system according to claim 1 further comprising a contact sensor carried by the cervical seal adapted to sense contact with a cervix of the patient and send signals of the contact or lack thereof to a controller.

9. The medical robot system according to claim 8 wherein the controller is configured to actuate the motor drive to move the cervical seal responsive to the signals of the contact from the contact sensor.

10. The medical robot system according to claim 8 wherein the contact sensor is at least one of a pressure sensor, capacitance sensor, impedance sensor, and optical sensor.

11. The medical robot system according to claim 1 further comprising a cervical canal sealing assembly coupled to at least one of the robotic arm and the endoscopic viewing assembly.

12. A medical robot system for use in intrauterine procedures, comprising:
    a robotic arm having a plurality of moveable arm segments;
    an endoscopic viewing assembly detachably coupled to a distal segment of the robotic arm, the endoscopic viewing assembly having an elongate endoscope shaft extending about a longitudinal axis to a distal end carrying an image sensor; and
    a stabilizing device detachably coupled to a distal segment of the robotic arm, the stabilizing device having an elongate tool shaft extending about a longitudinal axis adapted for engaging tissue to stabilize a cervix of a patient;
    a cervical canal sealing assembly coupled to at least one of the robotic arm and the endoscopic viewing assembly, where a distal end of the cervical canal sealing assembly comprises a cervical seal configured for movement co-axially with a medial portion of the elongate endoscope shaft; and
    a motor drive adapted for moving the cervical seal.

13. The medical robot system according to claim 12 further comprising a contact sensor carried by the cervical seal adapted to sense contact with a cervix of the patient and send signals of the contact or lack thereof to a controller.

14. The medical robot system according to claim 13 wherein the controller is configured to actuate the motor drive to move the cervical seal responsive to the signals of the contact from the contact sensor.

15. The medical robot system according to claim 13 wherein the contact sensor is at least one of a pressure sensor, capacitance sensor, impedance sensor, and optical sensor.

16. The medical robot system according to claim 12 further comprising an endoscope motor drive configured to rotate the elongate endoscope shaft relative to its longitudinal axis or configured to move the elongate endoscope shaft axially relative to its longitudinal axis.

17. The medical robot system according to claim 12 wherein the endoscopic viewing assembly carries a working channel extending therethrough.

18. The medical robot system according to claim 12 further comprising a tool motor drive configured to rotate the elongate tool shaft relative to its longitudinal axis or configured to move the elongate tool shaft axially relative to its longitudinal axis.

* * * * *